US00RE44822E

(19) United States
(12) Reissued Patent
Hechler et al.

(10) Patent Number: US RE44,822 E
(45) Date of Reissued Patent: Apr. 1, 2014

(54) PROCESS FOR HETEROGENEOUSLY CATALYZED PARTIAL DEHYDROGENATION OF AT LEAST ONE HYDROCARBON TO BE DEHYDROGENATED

(71) Applicant: BASF SE, Ludwigshafen (DE)

(72) Inventors: Claus Hechler, Ludwigshafen (DE); Wilhelm Ruppel, Mannheim (DE); Wolfgang Gerlinger, Limburgerhof (DE); Wolfgang Schneider, Bad Duerkheim (DE); Klaus Joachim Mueller-Engel, Stutensee (DE)

(73) Assignee: BASF SE, Ludwigshafen (DE)

(21) Appl. No.: 13/682,129

(22) Filed: Nov. 20, 2012

Related U.S. Patent Documents

Reissue of:
(64) Patent No.: 7,842,846
Issued: Nov. 30, 2010
Appl. No.: 11/678,362
Filed: Feb. 23, 2007

U.S. Applications:
(60) Provisional application No. 60/791,207, filed on Apr. 12, 2006, provisional application No. 60/787,165, filed on Mar. 30, 2006.

(30) Foreign Application Priority Data

Mar. 30, 2006 (DE) ..... 10 2006 015 235
Apr. 12, 2006 (DE) ..... 10 2006 017 623

(51) Int. Cl.
*C07C 5/48* (2006.01)

(52) U.S. Cl.
USPC ..... 585/658; 585/654; 585/656; 585/660; 422/236; 562/512.2; 562/523; 562/524; 568/470; 568/475; 568/476

(58) Field of Classification Search
USPC ..... 585/654, 656, 658, 660; 568/470, 475, 568/476; 562/512, 2, 523, 524; 422/236
See application file for complete search history.

(56) References Cited

U.S. PATENT DOCUMENTS 4,788,371 A 11/1988 Imai et al.
4,865,820 A * 9/1989 Dunster et al. ..... 422/220

(Continued)

FOREIGN PATENT DOCUMENTS

DE 199 37 107 2/2001
DE 102 11 275 9/2003

(Continued)

OTHER PUBLICATIONS

Composition of Air, CRC Handbook of Chemistry and Physics, 91st ed., 2011 Internet Version, D. R. Lide, ed.—month unknown.*

*Primary Examiner* — InSuk Bullock
*Assistant Examiner* — Bradley Etherton
(74) *Attorney, Agent, or Firm* — Oblon, Spivak, McClelland, Maier & Neustadt, L.L.P.

(57) ABSTRACT

A process for heterogeneously catalyzed partial dehydrogenation of a hydrocarbon, in which a reaction gas mixture input stream comprising the hydrocarbon to be dehydrogenated is conducted through a fixed catalyst bed disposed in a shaft and the reaction gas mixture input stream is obtained in the shaft by metering an input gas II comprising molecular oxygen upstream of the fixed catalyst bed into an input gas stream I which comprises molecular hydrogen and the hydrocarbon to be dehydrogenated and is flowing within the shaft toward the fixed catalyst bed.

46 Claims, 19 Drawing Sheets

(56) References Cited

U.S. PATENT DOCUMENTS

| | | | | |
|---|---|---|---|---|
| 4,886,928 | A | 12/1989 | Imai et al. | |
| 5,430,209 | A | 7/1995 | Agaskar et al. | |
| 5,527,979 | A | 6/1996 | Agaskar et al. | |
| 5,530,171 | A | 6/1996 | Agaskar et al. | |
| 5,563,314 | A | 10/1996 | Agaskar et al. | |
| 5,997,826 | A * | 12/1999 | Lodeng et al. | 422/634 |
| 6,670,303 | B1 | 12/2003 | Heineke et al. | |
| 6,781,017 | B2 | 8/2004 | Machhammer et al. | |
| 7,291,761 | B2 | 11/2007 | Machhammer et al. | |
| 2003/0060661 | A1 * | 3/2003 | Eck et al. | 562/600 |
| 2004/0073063 | A1 * | 4/2004 | Thiel et al. | 562/545 |
| 2005/0119515 | A1 * | 6/2005 | Machhammer et al. | 585/658 |
| 2006/0004226 | A1 | 1/2006 | Machhammer et al. | |
| 2006/0004227 | A1 | 1/2006 | Dieterle et al. | |
| 2006/0004229 | A1 | 1/2006 | Dieterle et al. | |
| 2006/0258529 | A1 | 11/2006 | Diefenbacher et al. | |
| 2007/0088092 | A1 | 4/2007 | Klanner et al. | |
| 2007/0099299 | A1 | 5/2007 | Simon et al. | |
| 2007/0117998 | A1 | 5/2007 | Machhammer et al. | |
| 2007/0123732 | A1 | 5/2007 | Dieterle et al. | |
| 2007/0142689 | A1 | 6/2007 | Hechler et al. | |

FOREIGN PATENT DOCUMENTS

| | | | | |
|---|---|---|---|---|
| DE | 10 2004 032 129 | | 3/2005 | |
| DE | 10 2005 009 885 | | 9/2006 | |
| DE | 10 2005 010 111 | | 9/2006 | |
| DE | 10 2005 013 039 | | 9/2006 | |
| DE | 10 2005 022 798 | | 11/2006 | |
| DE | 10 2005 044 916 | | 3/2007 | |
| DE | 10 2005 052 923 | | 5/2007 | |
| DE | 10 2005 057 197 | | 6/2007 | |
| DE | 10 2005 061 626 | | 6/2007 | |
| DE | 10 2005 052 917 | | 10/2007 | |
| EP | 0 799 169 | | 10/1997 | |
| WO | WO 01/96270 | | 12/2001 | |
| WO | WO 03/076370 | | 9/2003 | |
| WO | WO 03076370 | A1 * | 9/2003 | C07C 5/333 |
| WO | WO 2004/074222 | | 9/2004 | |
| WO | WO 2004074222 | A1 * | 9/2004 | C07C 5/48 |

* cited by examiner

PROCESS FOR HETEROGENEOUSLY CATALYZED PARTIAL DEHYDROGENATION OF AT LEAST ONE HYDROCARBON TO BE DEHYDROGENATED

Matter enclosed in heavy brackets [ ] appears in the original patent but forms no part of this reissue specification; matter printed in italics indicates the additions made by reissue.

The present invention relates to a process for heterogeneously catalyzed partial dehydrogenation of at least one hydrocarbon to be dehydrogenated to at least one dehydrogenated hydrocarbon, in which, for the purpose of the heterogeneously catalyzed partial dehydrogenation of the at least one hydrocarbon to be dehydrogenated, the entirety of a reaction gas mixture input stream comprising molecular oxygen, molecular hydrogen and the at least one hydrocarbon to be dehydrogenated is conducted through a fixed catalyst bed which is disposed in a shaft with predefined cross section and, in flow direction of the reaction gas mixture input stream, comprises first a bed of inert shaped bodies and a catalytically active bed which follows it in flow direction of the reaction gas mixture input stream and comprises at least one shaped catalyst body which is such that it, in the reaction gas mixture input stream in flow direction thereof, at least in its entrance region, causes a lower activation energy for the combustion reaction of molecular hydrogen with molecular oxygen to water and/or for the combustion reaction of hydrocarbon present in the reaction gas mixture input stream with molecular oxygen to give carbon oxides and water than for the dehydrogenation of the at least one hydrocarbon to be dehydrogenated to the at least one dehydrogenated hydrocarbon, with the proviso that a portion (generally at least 1 mol %, or at least 2 mol %, or at least 3 mol %, or at least 4 mol %, or at least 5 mol %) of the at least one hydrocarbon to be dehydrogenated is dehydrogenated to the at least one dehydrogenated hydrocarbon, and the reaction gas mixture input stream is obtained in the shaft by metering an input gas II comprising molecular oxygen with a total volume flow rate V2 upstream of the fixed catalyst bed to an input gas stream I which comprises molecular hydrogen and the at least one hydrocarbon to be dehydrogenated and is flowing within the shaft toward the fixed catalyst bed with a volume flow rate V1.

The present invention also relates to an apparatus for performing the process according to the invention and to processes for partial oxidation of the at least one dehydrogenated hydrocarbon.

The term "dehydrogenated hydrocarbon" used in this application is intended to comprise hydrocarbons whose molecules comprise at least two ("two" are preferred from a performance point of view) hydrogen atoms fewer than the molecules of a hydrocarbon to be dehydrogenated. Otherwise, the term hydrocarbon shall comprise substances whose molecules are composed only of the elements carbon and hydrogen.

Dehydrogenated hydrocarbons thus comprise in particular acyclic and cyclic aliphatic hydrocarbons having one or more C—C double bonds in the molecule.

Examples of such aliphatic dehydrogenated hydrocarbons are propene, isobutene, ethylene, 1-butene, 2-butene and butadiene. In other words, the dehydrogenated hydrocarbons include in particular the monounsaturated linear hydrocarbons (n-alkenes) or branched aliphatic hydrocarbons (e.g. isoalkenes), and also the cycloalkenes. The dehydrogenated hydrocarbons shall also comprise the alkapolyenes (e.g. dienes and trienes) which comprise more than one carbon-carbon double bond in the molecule. Dehydrogenated hydrocarbons shall also comprise hydrocarbon compounds which are obtainable starting from alkylaromatics such as ethylbenzene or isopropylbenzene by dehydrogenating the alkyl substituent. These are, for example, compounds such as styrene or $\alpha$-methylstyrene.

Quite generally, dehydrogenated hydrocarbons are valuable starting compounds for the synthesis of, for example, functionalized, free-radically polymerizable compounds (e.g. acrylic acid from propene or methacrylic acid from isobutene) and their polymerization products. For example, such functionalized compounds can be obtained by partial oxidation of dehydrogenated hydrocarbons. Dehydrogenated hydrocarbons are also suitable for preparing compounds such as methyl tert-butyl ether (subsequent product of isobutene which is suitable, for example, as a fuel additive for increasing the octane number). However, dehydrogenated hydrocarbons as such can also themselves be used for the polymerization.

In this document, useful hydrocarbons to be dehydrogenated are in particular the acyclic and cyclic alkanes, but also olefins (whose number of C—C double bonds is to be increased) (an example is the heterogeneously catalyzed partial dehydrogenation of n-butenes to butadiene).

In other words, the term "hydrocarbons to be dehydrogenated" in this document comprises, for example, hydrocarbons of the stoichiometry $C_nH_{2n+2}$ where n>1 to n≤20, and of the stoichiometry $C_nH_{2n}$ where n>1 to n≤20, and of the stoichiometry $C_nH_{2n-2}$ where n>2 to n≤20, and n=an integer, in particular $C_2$- to $C_{16}$-alkanes, for example ethane (to ethylene), propane (to propylene), n-butane, isobutane (to isobutene), n-pentane, isopentane, n-hexane, n-heptane, n-octane, n-nonane, n-decane, n-undecane, n-dodecane, n-tridecane, n-tetradecane, n-pentadecane and n-hexadecane.

In particular, though, all statements made in this document apply to $C_2$- to $C_6$-alkanes as hydrocarbons to be dehydrogenated and very particularly to $C_2$- to $C_4$-hydrocarbons (especially alkanes). In other words, hydrocarbons to be dehydrogenated in this document are in particular ethane, propane, n-butane and isobutane, but also 1-butene and 2-butene.

In this document, a heterogeneously catalyzed partial dehydrogenation of a hydrocarbon shall be understood to mean a (conventional) dehydrogenation in which free molecular hydrogen is formed at least as an intermediate and the dehydrogenation step accordingly proceeds endothermically (an exothermic hydrogen combustion can be included as a subsequent step). In contrast, in the case of a heterogeneously catalyzed partial oxydehydrogenation, the hydrogen to be pulled from the hydrocarbon to be dehydrogenated is pulled out directly as water ($H_2O$) by oxygen present. The dehydrogenation step of a heterogeneously catalyzed partial oxydehydrogenation therefore always proceeds exothermically.

In addition, a heterogeneously catalyzed partial dehydrogenation in this document shall be a dehydrogenation in a fixed catalyst bed.

Typically, a (conventional) heterogeneously catalyzed partial dehydrogenation of at least one hydrocarbon to be dehydrogenated (e.g. of propane) requires comparatively high temperatures. The achievable conversion is normally restricted by the thermodynamic equilibrium. Typical reaction temperatures are from 300 to 800° C., or from 400 to 700° C. One molecule of hydrogen is generated per molecule of, for example, propane dehydrogenated to propylene. High temperatures and removal of the $H_2$ reaction product shift the equilibrium position toward the at least one dehydrogenated hydrocarbon as the target product, as does lowering the partial pressure by inert dilution. In this document, inert gas (inert diluent gas) shall be understood generally to mean a reaction gas mixture constituent which behaves essentially chemically inertly under the conditions of the appropriate reaction and, considering each inert reaction gas mixture constituent alone, remains chemically unchanged to an extent of more than 95 mol %, preferably to an extent of more than 97 mol % or to an extent of more than 99 mol %. Examples of typical inert diluent gases are, for example, $N_2$, $H_2O$, $CO_2$, noble gases such as He, Ne and Ar, and mixtures of these gases, etc.

Since the dehydrogenation step in a heterogeneously catalyzed partial dehydrogenation of at least one hydrocarbon to be dehydrogenated (e.g. propane) to at least one dehydrogenated hydrocarbon proceeds endothermically, the heat (energy) required for the attainment of the required reaction temperature has to be supplied either to the reaction gas beforehand and/or in the course of the heterogeneously catalyzed dehydrogenation.

In the simplest manner, a heterogeneously catalyzed partial dehydrogenation can be carried out in a shaft reactor. A shaft (reactor) is a reaction chamber which is enclosed by a material shell which is in contact with the reaction chamber and has at least one first orifice for feeding of a reaction gas mixture into the reaction chamber and at least one second orifice for withdrawal of at least one product gas stream from the reaction chamber. In the reaction chamber (in the shaft) is disposed at least one fixed catalyst bed which is flowed through by the reaction gas mixture. During the residence time in the fixed catalyst bed, the desired partial dehydrogenation of the at least one hydrocarbon to be dehydrogenated to the at least one dehydrogenated hydrocarbon proceeds.

Appropriate dehydrogenation conversions are already achieved when the shaft (reactor) is thermally insulated from its environment (configured (quasi)adiabatically), the reaction gas mixture is heated to a temperature (starting temperature) of from 350 or 400 to 800° C. (frequently from 500 to 700° C., or from 550 to 650° C.), and the reaction gas mixture is conducted in only one adiabatic pass through at least one fixed catalyst bed disposed in the reaction chamber (in the shaft (reactor)).

Depending on conversion and selected inert dilution, the reaction gas in single pass through the fixed catalyst bed will cool by from about 30 to 200° C.

An additional use of steam as an inert diluent gas in the reaction gas mixture for a heterogeneously catalyzed partial dehydrogenation is advantageous for two reasons. Firstly, steam has a comparatively elevated molar heat capacity, which reduces the aforementioned cooling in the case of additional use.

In the case of reduced cooling, reduced starting temperatures are frequently also sufficient for the desired conversion. This is advantageous in that, in the course of heterogeneously catalyzed partial dehydrogenations of at least one hydrocarbon to be dehydrogenated, undesired side reactions form, to an extent increasing with increasing starting temperature, compounds including small amounts of high-boiling high molecular weight organic compounds (thermal decomposition products) up to and including elemental carbon, which are deposited on the catalyst surface and thus deactivated. Carbon which is nevertheless deposited on the catalyst surface is incidentally eliminated at least partly or fully and continuously by the principle of coal gasification at the elevated temperatures of a heterogeneously catalyzed partial dehydrogenation in the presence of steam as an inert diluent gas.

In an advantageous manner, a heterogeneously catalyzed hydrocarbon (e.g. propane) dehydrogenation can be conducted in an (externally preferably configured adiabatically) shaft reactor (both at dehydrogenation conversions based on a single pass of the reaction gas mixture through the reactor of ≤30 mol % and >30 mol % (e.g. up to 40 mol %, or up to 50 mol %, or up to 60 mol %)) when it is configured as a tray reactor.

A tray reactor comprises, in spatial succession, more than one fixed catalyst bed which catalyzes the dehydrogenation in the shaft (enclosed reaction chamber). The number of catalyst beds may, for example, be from 1 to 20, appropriately from 2 to 8 or from 3 to 6. In general, the fixed catalyst beds are arranged in radial or axial succession.

In a manner realizable in a particularly simple manner, the fixed catalyst beds are arranged in axial succession in the shaft along its axis pointing in flow direction of the reaction gas. However, they may also be arranged in the annular gaps of concentric cylindrical grids in the shaft. It is also possible to arrange the annular gaps in the shaft in segments one on top of another and to conduct the reaction gas, after it has passed radially within one segment, into the next segment above or below it.

On its way from one fixed catalyst bed to the next fixed catalyst bed, the reaction gas can then be subjected to intermediate heating (externally controlled temperature profile), for example by passing it through and/or over indirect heat exchangers (e.g. heat exchanger ribs or heat exchanger plates or heat exchanger tube bundles) mounted between the fixed bed trays in the shaft and operated by means of hot gases and/or liquids.

When the shaft reactor is otherwise configured adiabatically, it is generally sufficient for dehydrogenation conversions based on single pass of the reaction gas through the shaft reactor (e.g. propane→propylene conversions) of ≤40 mol % (for example in the case of use of the catalysts described in DE-A 10 2005 044 916 and in DE-A 19937107, especially those cited by way of example) to conduct the reaction gas mixture preheated to a temperature of from 350 or 400 or 450 to 550° C. (preferably from 400 to 500° C.) into the shaft (the enclosed reaction chamber accommodating the fixed catalyst beds) and, within the shaft, within the tray reaction chamber, to keep it at least within this temperature range by indirect heat exchange (externally controlled temperature profile). This is found to be particularly advantageous for the lifetime of the fixed catalyst beds up to their regeneration.

However, it is even more elegant from a performance point of view to perform the intermediate heating outlined above by a direct route (internally controlled temperature profile). To this end, a gas comprising molecular oxygen can be added in each case, advantageously to a restricted extent, to the reaction gas mixture (to the reaction gas) on its way through the shaft, for example after it passes through the first fixed catalyst bed in flow direction of the reaction gas and between the fixed catalyst beds downstream in flow direction of the reaction gas, which generates a reaction gas mixture stream comprising molecular oxygen, molecular hydrogen and at least one hydrocarbon to be dehydrogenated.

When the catalytically active bed downstream in flow direction of this reaction gas mixture stream, which comprises at least one shaped catalyst body, is configured (for example by suitable selection of the active composition) such that it (in the reaction gas mixture stream), in flow direction of the reaction gas mixture stream comprising the molecular oxygen, molecular hydrogen and the at least one hydrocarbon to be dehydrogenated, at least in its entrance region, causes a lower activation energy for the combustion reaction of molecular oxygen with molecular hydrogen to water and/or for the combustion reaction of hydrocarbon present in the reaction gas mixture stream to carbon oxides and water than for the dehydrogenation of the at least one hydrocarbon to be dehydrogenated, predominantly a restricted exothermic combustion of molecular hydrogen present in the reaction gas mixture and/or of hydrocarbon present in the reaction gas mixture with molecular oxygen (to $H_2O$ or $H_2O$ and carbon oxides) will initially proceed in the fixed catalyst bed as the reaction gas mixture passes through the fixed catalyst bed. The heat of reaction released heats the reaction gas mixture and can be consumed again in the course of the further passage, which is of predominantly endothermic and dehydrogenating character, of the reaction gas mixture through the fixed catalyst bed. The resulting combustion products such as $CO_2$, $H_2O$ and the $N_2$ which may, if appropriate, accompany the molecular oxygen required for the combustion form advantageous inert diluent gases.

Subsequently, before the reaction gas mixture which leaves the fixed catalyst bed and comprises molecular hydrogen formed beforehand enters the next fixed catalyst bed in flow direction of the reaction gas mixture, a gas comprising molecular oxygen can again be added thereto to a restricted extent, etc.

The weighting between "hydrogen combustion" and "hydrocarbon combustion" on entry of the reaction gas mixture comprising molecular oxygen, molecular hydrogen and at least one hydrocarbon to be dehydrogenated into the catalytically active bed can be influenced primarily by the selection of the catalyst in the entrance region (in flow direction of the reaction gas mixture) of the catalytically active bed. Useful catalysts which catalyze the combustion of molecular hydrogen and/or of hydrocarbon comparatively specifically (selectively) include, for example, those of the documents U.S. Pat. Nos. 4,788,371, 4,886,928, 5,430,209, 5,530,171, 5,527,979 and 5,563,314.

Preference is typically given to dominant "hydrogen combustion" over dominant "hydrocarbon combustion", since it causes both increased selectivity of the formation of the at least one dehydrogenated hydrocarbon compound and increased dehydrogenation conversion based on a single pass of the reaction gas through the tray reactor. This is generally the case when the catalytically active bed comprises, as catalysts, only dehydrogenation catalysts (especially those recommended in DE-A 19 937 107 (especially the exemplary catalysts of this DE-A), since they are generally capable of catalyzing not only the dehydrogenation of the hydrocarbon to be dehydrogenated (e.g. propane) but also the combustion of molecular hydrogen and of hydrocarbons with molecular oxygen. In the case of a competition situation, the hydrogen combustion proceeds very much more rapidly over these catalysts both in comparison to the dehydrogenation of the at least one hydrocarbon to be dehydrogenated (e.g. propane) and in comparison to, for example, its combustion (i.e. the catalysts require by far the lowest activation energy for the combustion of molecular hydrogen under the given conditions).

Depending on the extent of the combustion reaction performed (i.e. also depending upon the amount of molecular oxygen supplied), the overall reaction profile in single pass of the reaction gas mixture through the tray reactor, with regard to the integral thermal character (i.e. with regard to the net thermal character), may be configured either endothermically (negative) or autothermally (essentially zero) or exothermically (positive).

The combustion of molecular hydrogen affords about twice that amount of heat which is consumed for its formation in the course of the dehydrogenation.

It is of course also possible, between two fixed catalyst beds, to make use of the principle of internal temperature control and of the principle of external temperature control. The isothermicity of a heterogeneously catalyzed partial dehydrogenation of at least one hydrocarbon can also be improved further by incorporating closed (for example tubular) internals which have favorably, but not necessarily, been evacuated before being inserted between the fixed catalyst beds in the tray reaction chamber. Such internals may also be placed into the particular fixed catalyst bed. These internals comprise suitable solids or liquids which evaporate or melt above a certain temperature and consume heat in doing so, and condense again where the temperature goes below this level and release heat in doing so. In principle, fluid (gaseous and/or liquid) heat carriers may additionally be conducted outside the material shell of the shaft reactor in order to further improve the isothermicity. However, the level of application complexity is considerable, which is why preference is generally given to the external adiabatic configuration.

It will be appreciated that the measure of internal temperature control described can also be employed in order to heat the reaction gas mixture fed to the first fixed catalyst bed in flow direction of the reaction gas mixture to the required reaction temperature. For this purpose, molecular hydrogen from another source may, if appropriate for the purpose, be supplied beforehand to the reaction gas mixture which comprises the at least one hydrocarbon to be dehydrogenated and is conducted into the shaft reactor. However, it is also possible to dispense with such a hydrogen addition. In that case, the internal temperature control can be effected essentially only by hydrocarbon combustion. Frequently, the reaction gas mixture fed to the first fixed catalyst bed can also be brought to reaction temperature in another way. For example, the starting gas streams from which the reaction gas mixture fed to the first fixed catalyst bed is constituted may already have appropriate temperatures. These starting gas streams too may already comprise molecular oxygen, so that the problem of metering a gas comprising molecular oxygen to a gas mixture flowing to the first fixed catalyst bed in flow direction in the shaft does not occur.

In principle, processes for heterogeneously catalyzed partial dehydrogenation of at least one hydrocarbon to be dehydrogenated to at least one dehydrogenated hydrocarbon in a shaft reactor configured to a fixed bed tray reactor with internally controlled temperature profile are known (cf., for example, DE-A 102005061626, DE-A 102005057197, DE-A 102005052923, DE-A 102005052917, DE-A 102005022798, DE-A 102005009885, DE-A 102005010111, DE-A 102004032129, DE-A 102005013039, WO 03/076370, DE-A 10 211 275, WO 01/96270 and the prior art cited in these documents).

The aforementioned documents also disclose the configuration of the individual fixed catalyst bed of the tray reactor such that the actual catalytically active bed which comprises at least one catalytically active shaped catalyst body is covered in flow direction of the reaction gas mixture stream with a bed of inert shaped bodies and the metered addition of the gas which comprises molecular oxygen and is required for the internal temperature control to the gas stream which comprises molecular hydrogen and the at least one hydrocarbon to be dehydrogenated and flows to such a fixed catalyst bed before this gas stream has reached the fixed catalyst bed (i.e. the inert bed (bed of inert shaped bodies) which covers the actual catalytically active bed).

However, the acknowledged prior art leaves entirely open in what manner (i.e. how) the metered addition of the gas stream comprising molecular oxygen is to be undertaken (performed) on the industrial scale.

The manner of the feeding of the gas stream comprising molecular oxygen to the gas stream which comprises molecular hydrogen and at least one hydrocarbon to be dehydrogenated flowing toward the relevant fixed catalyst bed in the shaft is, according to in-house experimental results, however, relevant to industrial scale process procedures for various reasons.

Firstly, there are locally elevated oxygen concentrations where the gas comprising molecular oxygen is metered in. In unfavorable cases, these may be such that ignitable (explosive) gas mixtures are formed locally, which is undesired from an application point of view, which is why their existence should be brief at most and be tightly restricted locally. Moreover, the reaction gas mixture which results after the metered addition already has an elevated temperature prior to the desired heterogeneously catalyzed combustion (and is increased additionally in the course of the heterogeneously catalyzed combustion). Before the reaction gas mixture comprising molecular oxygen reaches the fixed catalyst bed, there are therefore normally undesired homogeneous free-radical reactions within the reaction gas mixture (for example undesired exothermic homogeneous free-radical partial oxidations and/or oxydehydrogenations of hydrocarbon; the heats of reaction evolved locally by these undesired reactions bring about local temperature increases whose consequence is typically an increase in undesired thermal decompositions of hydrocarbons) with a broad by-product spectrum which reduce the target product selectivity and generally also the catalyst lifetime. Such a reduced target product selectivity is disadvantageous especially when the at least one target product, the at least one dehydrogenated hydrocarbon, is to be subjected to a subsequent reaction (for example to a heterogeneously catalyzed partial oxidation). Within the fixed catalyst bed, such undesired free-radical side reactions are substantially suppressed, since the large inner surface of the fixed bed charge functions as a free-radical scavenger. The extent of such undesired free-radical reactions generally increases exponentially with the available reaction time.

For this reason, it has already been proposed to undertake the metered addition of the gas comprising molecular oxygen exclusively directly into the inert bed covering the catalytically active bed. However, such a procedure is disadvantageous in that, in the case of distribution of the gas comprising molecular oxygen into the inert bed, a centrally fed distribution system (for example a line system with exit orifices) in the inert bed meets locally essentially randomly distributed distribution resistances (depending on in what way and whether or to what extent an inert shaped body blocks the particular exit orifice of the line system). This leads in an undesired manner to locally, in some cases comparatively different, feed streams of the gas comprising molecular oxygen. In the most unfavorable case, this can lead, in the case of a feed of the gas comprising molecular oxygen controlled according to the total amount fed per unit time, to no gas comprising molecular oxygen exiting from the exit orifice at some exit orifices, but rather gas comprising molecular hydrogen and at least one hydrocarbon to be dehydrogenated entering the exit orifice. Moreover, the inert shaped bodies can unfavorably influence the flow direction of the individual metering streams exiting from the exit orifices and, in the extreme case, even conduct the local metering out of the fixed catalyst bed.

When the reaction gas mixture comprising metered molecular oxygen enters the actual catalytically active bed disposed beyond the inert bed in flow direction, an inhomogeneous distribution of the molecular oxygen in the reaction gas mixture causes local catalyzed combustions of a different degree in the catalytically active bed. These are accompanied by correspondingly different local evolutions of heat. Locally elevated temperatures normally cause accelerated local aging of the catalytically active bed. Although it is possible with an inert bed expanded to a maximum degree in flow direction of the reaction gas mixture to achieve an essentially homogeneous distribution of the molecular oxygen at the entrance of the reaction gas mixture into the catalytically active bed, an increasing expansion of the inert bed is accompanied by an increasing pressure drop of the reaction gas mixture as it passes through the bed, which ultimately entails increased compressor output. With increasing residence time of the reaction gas in the inert bed, undesired side reactions can also again come into effect. This is especially true when the inner surface area of the inert bed is comparatively restricted.

It is therefore an object of the present invention to provide a process as described in the preamble of this document, which takes account of the aforementioned features in a highly comprehensive and highly economic, i.e. simple and relatively uncomplicated, manner, and enables minimization of the expansion of the relevant inert bed. The teaching of U.S. Pat. No. 2,584,391 is incapable of solving the problem stated, since it is directed to a process in a catalytic fluidized bed.

The teaching of DE-A 102 004 024 957 is likewise incapable of solving the problem stated. Firstly, it is directed to a heterogeneously catalyzed oxydehydrogenation in which the reaction gas mixture comprising molecular oxygen is fed directly into the catalytically active bed, and additionally with discontinuities in the feed system. Moreover, it requires a tube bundle system which is comparatively complicated to manufacture and has expensive tube plates.

WO 2004/074 222 is equally unhelpful in solving the problem stated. Thus, this document requires that the gas comprising the molecular oxygen and the gas stream comprising the at least one hydrocarbon to be dehydrogenated be conducted in strictly parallel flow control with respect to one another, which requires a comparatively complex apparatus. In addition, a parallel flow combination requires a comparatively long mixing zone.

DE-A 102 004 003 070 is likewise incapable of contributing to the solution of the problem stated, since it is directed to a heterogeneously catalyzed oxydehydrogenation in which the reaction gas mixture is conducted directly to the catalytically active bed.

A solution proposed to the problem unsolved in the prior art is therefore a process for heterogeneously catalyzed partial dehydrogenation of at least one hydrocarbon to be dehydrogenated to at least one dehydrogenated hydrocarbon, in which, for the purpose of the heterogeneously catalyzed partial dehydrogenation of the at least one hydrocarbon to be dehydrogenated, the entirety of a reaction gas mixture input stream comprising molecular oxygen, molecular hydrogen and the at least one hydrocarbon to be dehydrogenated is conducted through a fixed catalyst bed which is disposed in a shaft with predefined cross section and, in flow direction of the reaction gas mixture input stream, comprises first a bed of inert shaped bodies and a catalytically active bed which follows it in flow direction of the reaction gas mixture stream and comprises at least one shaped catalyst body which is such that it, in the reaction gas mixture input stream in flow direction thereof (of the reaction gas mixture input stream), at least in its entrance region, causes a lower activation energy for the combustion reaction of molecular hydrogen with molecular oxygen to water and/or for the combustion reaction of hydrocarbon present in the reaction gas mixture input stream with molecular oxygen to give carbon oxides and water than for the dehydrogenation of the at least one hydrocarbon to be dehydrogenated to the at least one dehydrogenated hydrocarbon, with the proviso that a portion (generally at least 1 mol %, or at least 2 mol %, or at least 3 mol %, or at least 4 mol %, or at least 5 mol %) of the at least one hydrocarbon to be dehydrogenated is dehydrogenated to the at least one dehydrogenated hydrocarbon, and the reaction gas mixture input stream is obtained in the shaft by metering an input gas II comprising molecular oxygen with a total volume flow rate V2 upstream of the fixed catalyst bed to an input gas stream I which comprises molecular hydrogen and the at least one hydrocarbon to be dehydrogenated and is flowing within the shaft toward the fixed catalyst bed with the volume flow rate V1, wherein the input gas II is metered in the form of input gas II streams flowing out of a plurality of exit orifices A of a line system disposed upstream of the fixed catalyst bed in flow direction of the input gas stream II such mat (a) the directions of the majority M of all input gas II streams exiting from the exit orifices A in the theoretical absence of the input gas stream I enclose an angle $\alpha$ of 90±60° with the flow direction of the input gas stream I;

(b) the distance D of the majority M of all exit orifices A from the fixed catalyst bed, based on the flow rate W of the input gas stream I in the shaft, is less than or equal to the induction time J of the reaction gas input mixture (this is the gas mixture that constitutes the reaction gas mixture input stream) multiplied by 2·W;

(c) a projection of the centers of the majority M of all exit orifices A in flow direction of the input gas stream I into the projection plane E at right angles to the flow direction of the input gas stream I within the projection plane E gives rise to a number ZA of the exit orifice centers present in any m2 of ≥10 for at least 75% (preferably for at least 80%, better for at least 85%, or for at least 90%, advantageously for at least 95% or even better for 100%) of the projection area covered by the input gas stream I;

d) the individual input gas II streams (e.g. volume streams or mass streams) exiting from the exit orifices A corresponding to the number ZA of exit orifice centers deviate from their numerical mean by not more than 50% (with the numerical mean as the reference basis);

e) among the number ZA of exit orifices, the distance d from one exit orifice center to the closest (in the projection plane E) exit orifice center is not more than $2\sqrt{1m^2/ZA}$, and f) the V1:V2 ratio is ≥8.

In principle, the input gas II (for example in the case of air) in the process according to the invention can be metered in at, for example, 20° C. (outside temperature).

Appropriately in accordance with the invention (which ensures a more uniform gas density over the exit orifices A), the temperature difference $\Delta T_{II}^{I}$ (in magnitude) between the temperature of the input gas stream I and of the input gas II should, however, not be greater than 300° C. $\Delta T_{II}^{I}$ is preferably not greater than 250° C., more preferably not greater than 200° C., advantageously not greater than 150° C., particularly advantageously not greater than 100° C., very particularly preferably not greater than 75° C., very particularly advantageously not greater than 50° C., better not greater than 30° C. and at best ≤20° C., or ≤10° C. or 0° C.

When the two temperatures are not identical, the input stream I generally has the higher temperature.

The aforementioned is especially true when the input stream I has a temperature of ≥350° C. (e.g. ≥375° C., or ≥400° C., or ≥425° C., or ≥450° C., or ≥475° C., or ≥500° C., or ≥525° C., or ≥550° C., or ≥600° C.). In general, this temperature will be ≤800° C., frequently ≤700° C.

The fixed catalyst bed disposed in the shaft in the process according to the invention may be the sole fixed catalyst bed disposed in a shaft reactor or be one of a plurality of catalyst beds in a shaft reactor configured as a tray reactor. When the fixed catalyst bed is the first in flow direction of the reaction gas in a shaft reactor, the reaction gas mixture input stream will generally not yet comprise any dehydrogenated hydrocarbon. When the fixed catalyst bed in the process according to the invention is, however, a fixed catalyst bed which follows this first fixed catalyst bed in flow direction of the reaction gas, the reaction gas mixture input stream (this is the gas stream conducted into this fixed catalyst bed) will normally, however, also comprise some of the at least one dehydrogenated hydrocarbon. The fixed catalyst bed in the process according to the invention may also be the last fixed catalyst bed in a tray reactor in flow direction of the reaction gas.

In other words, the process according to the invention may in principle be applied to all fixed catalyst beds disposed in a tray reactor.

However, the reaction gas input mixture fed to a first fixed catalyst bed disposed in a shaft reactor in flow direction of the reaction gas may already comprise some of the at least one dehydrogenated hydrocarbon for various reasons. This is the case, for example, when, according to the procedure described in WO 03/076 370 or DE-A 102 112 75, the product gas stream exiting from the dehydrogenation reactor is divided into two portions of identical composition and one of the two portions is recycled as dehydrogenation cycle gas into the reaction gas mixture fed to the dehydrogenation reactor and the other portion is used further in another way (for example for the purpose of a heterogeneously catalyzed partial oxidation of dehydrogenated hydrocarbon formed in the reaction chamber).

The aforementioned also applies correspondingly to the input gas stream I which, together with the input gas II comprising molecular oxygen in the process according to the invention, constitutes the reaction gas mixture input stream fed to the fixed catalyst bed.

Useful input gas II for the process according to the invention is in principle either molecular oxygen in pure form or a mixture of molecular oxygen and inert gas (e.g. air). Such inert gases used may, for example, be molecular nitrogen, carbon dioxide, noble gases and/or steam.

Appropriately for the application, the input gas II will be a mixture of air and steam. The use of mixtures of molecular oxygen and inert gas as input gas II is advantageous over use of pure molecular oxygen as input gas II in that this makes the explosion behavior in the region of the exit orifices A on entry of the input gas II into the input gas stream I more favorable. Moreover, additional use of inert gas in the input gas II enables larger total volume flow rates V2, which is found to be advantageous for the stability (uniformity) of metering of input gas II into the input gas stream I. When, however, increased inert gas contents in the product gas stream of a heterogeneously catalyzed partial dehydrogenation of at least one hydrocarbon are undesired (for example when they are found to be ballast which has to be conveyed at high cost in the subsequent use of the at least one dehydrogenated hydrocarbon), their content in the input gas II will be minimized.

Input gases II suitable for the process according to the invention may, for example, have the following contents:

from 0 to 80% by volume of steam,
from 10 to 97% by volume of $N_2$ and
from 3 to 25% by volume of $O_2$.

Possible input gas II contents may thus be:

from 15 to 80% by volume of $H_2O$,
from 20 to 85% by volume of $N_2$ and
from 5 to 25% by volume of $O_2$;

or from 15 to 60% by volume of $H_2O$,
from 20 to 80% by volume of $N_2$, and
from 5 to 20% by volume of $O_2$.

The ratio of the volume flow rate V1 (in $m^3$ (STP)/h; $m^3$ (STP) are the volume in $m^3$ that the appropriate amount of gas would take up under standard conditions (0° C., 1 atm)) to the total volume flow rate V2 (likewise in $m^3$ (STP)/h) in the process according to the invention is ≥8. It is preferably ≥10, more preferably ≥15 and most preferably ≥20. The V1:V2 ratio in the process according to the invention is frequently also ≥25 or ≥30, or ≥40 or ≥50. In general, the V1:V2 ratio in the process according to the invention will, however, be ≤500, frequently ≤400 or ≤300, in many cases also ≤200 or ≤100.

In general, the fixed catalyst bed in the process according to the invention has, in flow direction of the reaction gas mixture, not only a cover layer of inert material but also a final layer of inert shaped bodies. This is because, for example, in the case of an axial tray reactor, the fixed catalyst bed is generally supported by a gas-permeable grid whose mesh size frequently has a larger dimension than the shaped catalyst bodies.

When the fixed catalyst bed disposed in the shaft in the process according to the invention is the first (and if appropriate only) fixed catalyst bed in flow direction of the input gas stream I in a shaft reactor, the input gas stream I flowing with the volume flow rate V1 in the shaft normally corresponds to the input gas stream fed to the shaft reactor for the purpose of the heterogeneously catalyzed dehydrogenation of the at least one hydrocarbon to be dehydrogenated. It generally comprises ≥5% by volume of the at least one hydrocarbon to be dehydrogenated (e.g. propane). In addition, it may comprise, for example:

a) $N_2$;
b) $N_2$ and $H_2O$;
c) $N_2$, $H_2O$ and $H_2$;
d) $N_2$, $H_2O$, $CO_2$ and $H_2$; or
e) $N_2$, $H_2O$, CO, $CO_2$ and $H_2$.

In addition, it may also already comprise limited amounts of molecular oxygen.

When the fixed catalyst bed of the process according to the invention is, however, a fixed catalyst bed which follows this first fixed catalyst bed in flow direction of the reaction gas, the input gas stream I will normally correspond to the reaction gas mixture exiting from the preceding fixed catalyst bed in flow direction of the reaction gas, which will normally comprise at least one dehydrogenated hydrocarbon in addition to the aforementioned gases. In general, it will then comprise essentially no molecular oxygen.

The majority M of all exit orifices A (and of the individual input gas II streams exiting from them) is understood in this document to mean those exit orifices A (and the individual input gas II streams exiting from them) from which a total of just more than 50% (preferably just more than 60 or 70%, more preferably just more than 80 or 90% and most preferably 100%) of the total volume flow rate V2 exit, with the proviso that the individual input gas II streams exiting from them, among the entirety of all individual input gas II streams, comprise none which is smaller than the largest of the individual input gas II streams *not* included in this majority M.

Preferably in accordance with the invention, the individual input gas II streams exiting from the exit orifices A are, as far as possible in the context of what is possible in manufacturing, equally large.

In principle, the geometry of the exit orifices A in the process according to the invention is arbitrary. In other words, both polygonal (e.g. triagonal, tetragonal, pentagonal, hexagonal, etc.) and round (e.g. elliptical or circular) exit orifices A are possible. The geometry of all exit orifices A in the process according to the invention is preferably uniform (including their size). Round exit orifices A ("holes") are preferred in accordance with the invention. The longest dimension L (their diameter in the case of circular exit orifices) of an exit orifice A (this is the longest line directly connecting two points on the outline of the particular exit orifice A) in the process according to the invention is advantageously from ≥1.0 mm to ≤5 cm. In other words, possible values for L are from ≥0.2 mm to ≤4 cm, and from ≥0.3 mm to ≤3 cm, or from ≥0.4 mm to ≤2 cm, or from ≥0.5 mm to ≤1 cm, in many cases from ≥1 mm to ≤5 mm.

The (cross-sectional) areas of the exit orifices A are preferably in the regions of $(\pi \cdot L^2)/2$, where the values of the aforementioned ranges are to be inserted for L.

When the ratio R formed from the longest dimension L of an exit orifice A* and the shortest dimension K of this exit orifice A* (this is the shortest line connecting two points on the outline of the exit orifice A* and leading through the center of the exit orifice A*), i.e. R=L:K, is ≥5 (normally, R is <5 and ≥1), this exit orifice A* (for example when the exit orifice A* is a slot) should, for all purposes of the present invention, be replaced theoretically by a number n of uniform virtual circular exit orifices A which is calculated as follows:

$$n = \frac{U^2}{4\Pi \cdot F}$$

where

π=the ratio of the circle circumference to the circle diameter,
U=circumference of the exit orifice A*, and
F=exit surface area of the exit orifice A*.

When n is not an integer, it is rounded to the closest whole number (in the case of 1.50 and its analogs, the number is rounded up).

The diameter $d_h$ of the aforementioned virtual exit orifices A is calculated as follows:

$$d_h = \frac{4 \cdot F}{U}$$

It is referred to as the hydraulic diameter of the exit orifice A*.

The centers of these virtual circular exit orifices A should be disposed on a straight line G whose length corresponds to the longest dimension L and which leads through the center of the exit orifice A* such that this center halves the length of the straight line G and at least the lengthened straight line G cuts the outline of the exit orifice A* twice and the straight line G encloses a right angle with the flow direction of the input stream I. The centers of the n virtual exit orifices should be distributed uniformly on this straight line G, the center of the exit orifice A* itself forming the midpoint (the center) of this distribution.

The wording "in the theoretical absence" of the input gas stream I expresses that an (individual) input gas II stream exiting from an exit orifice A in the process according to the invention changes direction when it combines with the input gas stream I. The angle $\alpha$ is therefore determined by employing the direction of the (individual) input gas II stream exiting from the particular exit orifice A that would be present were the input gas stream I to be suppressed under otherwise unchanged process conditions.

Advantageously in accordance with the invention, for the majority M of all exit orifices A (or of the input gas II streams exiting from them), the angle $\alpha$ is 90±50°, preferably 90±40°, more preferably 90±30°, better 90±20°, even more preferably 90±10°, even better 90±5° and at best in all cases 90°. The direction of the (individual) input gas II stream exiting from the exit orifice should be the direction of the exiting central jet.

According to the invention, the exit orifices A should be disposed upstream of the fixed catalyst bed. In other words, the exit orifices A should not be blocked by inert shaped bodies. Instead, a jet drawn from the center of the exit orifice A at right angles to the flow direction of the input stream I should appropriately not come into contact with any inert shaped body at least for a jet length of two (preferably at least four, more preferably at least six and most preferably at least eight) hydraulic diameters $d_h$ of the exit orifice A ($d_h$=4.F/U) and at best for any jet length. Otherwise, it is advantageous in accordance with the invention when the exit orifices A are disposed as close as possible to the fixed catalyst bed.

In this document, the distance D of an exit orifice A from the fixed catalyst bed shall be the shortest direct line connecting the center of the exit orifice to any point of contact with an inert shaped body in the inert cover bed of the fixed catalyst bed.

According to the invention, the distances D of the majority M of all exit orifices A from the fixed catalyst bed, based on the flow rate W (in m/s) of the input gas stream I (=volume flow rate of the input gas stream I divided by the narrowest cross-sectional area flowed through by this volume stream (this is the area in a plane at right angles to the input gas stream I which is covered by the input gas stream I and through which the input gas stream I flows, with the proviso that centers of exit orifices A are present in the aforementioned plane)) in the shaft, should be less than or equal to the induction time J (in s) of the reaction gas input mixture multiplied by 2·W. In other words, the majority M of all exit orifices A should satisfy: $D \leq 2 \cdot W \cdot J$.

The induction time J shall be understood to mean the following.

When an induction gas mixture which has the same content of molecular oxygen and of hydrocarbon to be dehydrogenated (in each case in % by volume) as the reaction gas mixture input stream and which is obtained by adding the molecular oxygen as starting gas 2 in the form of air (or as pure molecular oxygen or as a mixture thereof with molecular nitrogen) to the hydrocarbon to be dehydrogenated (or a mixture thereof with molecular nitrogen) as starting gas 1 (i.e. the induction gas mixture comprises, as gases other than molecular oxygen and hydrocarbon to be dehydrogenated, only molecular nitrogen), and which is at the same temperature $T^R$ and the same pressure $P^R$ as are present in the reaction gas mixture input stream is left alone, the oxygen content ($O_2$) present in this induction gas mixture decreases as a function of time. The induction time J of the reaction gas mixture input stream is that time within which the oxygen content of the accompanying induction gas mixture has fallen to 70% of its starting content (as an absolute amount).

The experimental determination of the induction time J is possible in a simple manner as follows.

A Y-shaped mixing nozzle manufactured from quartz glass (inner tube diameter: 0.6 cm; wall thickness: 1 mm; angle of fork=90°; the two branches of the fork are coiled and each have a straight length of 2 m; the quartz tube of the Y-shaped mixing nozzle supporting the fork has a length of 0.5 m) is introduced into an oven (for example a radiative oven or a forced-air oven) in which it is heated to the temperature $T^R$. The starting gas 1 is introduced into one of the two branches of the fork and the starting gas 2 is fed into the other of the two branches of the fork. At the end of the quartz tube of the Y-shaped mixing nozzle bearing the fork is disposed a reducing valve which opens at the pressure $P^R$. The volume flow rates of the two starting gases relative to one another are such that the desired induction gas mixture composition forms beyond the fork. The absolute volume flow rates are adjusted such that the oxygen content of the induction gas mixture on exit from the carrier tube of the Y-shaped mixing nozzle is only 70% of its calculable starting content. J is calculated from the flow rate and the length of the quartz tube bearing the fork as the quotient of the length divided by the flow rate. In general, the volume flow rate of the induction gas mixture in the carrier tube of the Y-shaped mixing nozzle will be <10 $m^3/h$. The oxygen content of the induction gas mixture stream at the exit from the carrier tube of the Y-shaped mixing nozzle can be determined by means of a lambda probe ($\lambda$ probe). This may be designed as a Nernst probe. This is a ceramic sensor element of which one side is exposed to the induction gas mixture stream and the other side to an oxygen reference. For example, ambient air may be used as such a reference. At the elevated temperatures $T^R$, the customarily used yttrium-doped zirconium dioxide ceramic of the probe becomes conducting for negative oxygen ions. The concentration difference of molecular oxygen in the two gases generates ion diffusion in the probe. This allows an electrical current to be abstracted between platinum electrodes mounted inside and outside the probe, the probe voltage. This voltage is described by the Nernst equation and is a direct measure of the oxygen content of the induction gas mixture stream at the exit from the carrier tube of the Y-shaped mixing nozzle.

Alternatively, a lambda resistance probe can be used. The sensor element here generally consists of a semiconducting titanium dioxide ceramic. The charge carriers are provided by oxygen defects which act as donors. With surrounding oxygen, the defect sites are occupied and the number of free charge carriers is reduced. The oxygen ions do not make a substantial contribution here to the conductivity, but rather the oxygen reduces the number of free charge carriers. At high oxygen concentration, the sensor material has a high resistance. The signal is generated by a voltage divider with a fixed resistance.

Manufacturers of lambda probes are, for example, Robert Bosch GmbH, and also Denso and NGK.

In this document, the center of an exit orifice shall be understood to mean the theoretical center of mass of the exit orifice (in homogeneous mass filling).

Preferably in accordance with the invention, the condition $D \leq 1 \cdot W \cdot J$, better $D \leq 0.5 \cdot W \cdot J$, shall be fulfilled for the majority M of all exit orifices A. Most preferably, the condition $D \leq 0.2 \cdot W \cdot J$ shall be valid for the majority of all exit orifices A. It is even better when the condition $D \leq 0.05 \cdot W \cdot J$ is satisfied for the plurality M of all exit orifices A. Very particularly advantageously, all exit orifices A always satisfy the relevant condition. It is also favorable in accordance with the invention when all exit orifices A have a uniform value for D.

However, all exit orifices A need not necessarily have a uniform value for D.

However, when the centers of the majority M of all exit orifices A in flow direction of the input gas stream I are projected into the projection plane E at right angles to the flow direction of the input gas stream I, the number ZA of exit orifice centers present in any $m^2$ must, in accordance with the invention, be ≥10 for at least 75% (preferably for at least 80%, better for at least 85%, even better for at least 90%, preferably for at least 95%, and more preferably for 100%) of the projection surface area covered by the input gas stream I within the projection plane E. Advantageously in accordance with the invention, the aforementioned ZA is ZA≥20 or ≥30, preferably ≥40 or ≥50, more preferably ≥60 or ≥70, most preferably ≥80 or ≥90 or ≥100. Advantageously in accordance with the invention, ZA is selected to be large (an increasing ZA is generally accompanied by decreasing longest dimensions L of the exit orifices A). In principle, ZA in the process according to the invention may be up to 100 000 and more. However, for reasons of economically viable manufacture, ZA will generally usually be ≤10 000, frequently ≤1000.

Among the number ZA of exit orifices, the distance d from one exit orifice center to the closest exit orifice center (in the projection plane E) should not be more than $2\sqrt{1m^2/ZA}$.

In other words, in accordance with the invention, d cannot be more than $1.75\sqrt{1m^2/ZA}$, or more than $1.5\sqrt{1m^2/ZA}$, or more than $1.25\sqrt{1m^2/ZA}$.

Of course, the number ZA of exit orifice centers may also be distributed uniformly ($d=\sqrt{1m^2/ZA}$) over the projection surface area covered by the input gas stream I in the projection plane E.

It is also favorable in accordance with the invention when no exit orifices for which the input gas II streams exiting from these exit orifices A are directed counter to one another are opposite one another.

It is also essential in accordance with the invention that the individual input gas II (e.g. volume or mass) streams exiting from the exit orifices A corresponding to the number ZA of exit orifice centers do not deviate by more than 50% (preferably by not more than 40%, more preferably by not more than 30%, even more preferably by not more than 20% or by not more than 10%, even better by not more than 5% and at best not at all) from their numerical mean (averaged over the number ZA). The numerical mean is the reference basis.

Advantageously in accordance with the invention, the shaft in the process according to the invention has an (undeviating) straight cylindrical geometry (two coincident (congruent) base surfaces which lie within parallel planes and whose points are connected by parallel, vertical lines on the two base surfaces). Within the cylindrical geometries, preference is given to the elliptical cylinder and in particular to the circular cylinder.

Of course, the process according to the invention is also used by those which, in addition to the inventive injection of a gas comprising molecular oxygen upstream of the fixed catalyst bed, also undertake metered addition of a gas comprising molecular oxygen into the inert cover bed.

A further inventive requirement is that, based on the single pass of the reaction gas mixture input stream through the fixed catalyst bed, a portion, generally at least 1 mol %, or at least 2 mol %, or at least 3 mol %, or at least 4 mol %, or at least 5 mol % (preferably at least 7 mol %, more preferably at least 9 mol % and most preferably at least 11 mol %) of the at least one hydrocarbon to be dehydrogenated present in the reaction gas mixture input stream is dehydrogenated to the at least one dehydrogenated hydrocarbon. However, the aforementioned molar percentage will normally be ≤20 mol %.

Generally, the reaction gas mixture input stream will generally comprise at least 5% by volume of the at least one hydrocarbon to be dehydrogenated. Frequently, this volume fraction will be at values on the same basis of ≥10% by volume, often ≥15% by volume and usually ≥20% by volume or ≥25% by volume, or ≥30% by volume. In general, this volume fraction, however, will be at values on the same basis of ≤90% by volume, usually ≤80% by volume and often ≤70% by volume. The above statements apply (like all other statements in this document) especially in the case of propane as the hydrocarbon to be dehydrogenated and propylene as the dehydrogenated hydrocarbon. Of course, they also apply when isobutane is the hydrocarbon to be dehydrogenated and isobutene is the dehydrogenated hydrocarbon.

In general, the amount of input gas II metered into the input gas stream I in the process according to the invention will be such that the resulting reaction gas input mixture, based on the amount of hydrocarbon to be dehydrogenated and dehydrogenated hydrocarbon (e.g. propane and propylene) present therein, comprises from 0.01 or 0.5 to 30% by volume of molecular oxygen.

Appropriately in accordance with the invention, the molar content of molecular oxygen in the reaction gas mixture input stream is not more than 50% of the molar amount of molecular hydrogen present therein.

In general, the molar content of molecular oxygen in the reaction gas mixture input stream, based on the molar amount of molecular hydrogen present therein, is from 10 to 40 mol %, frequently from 15 to 35 mol % and in many cases from 20 to 30 mol %.

Advantageously in accordance with the invention, in the process according to the invention, the entirety (or at least 95 mol %) of the molecular oxygen present in the reaction gas mixture input stream is consumed as the reaction gas mixture input stream passes through the fixed catalyst bed for the consumption of the molecular hydrogen present in the reaction gas mixture input stream.

Appropriately from an application point of view, in the process according to the invention, about half of the amount of molecular hydrogen which, in the case of a tray reactor, has been formed in the fixed catalyst bed flowed through beforehand is combusted with molecular oxygen as the reaction gas mixture input stream passes through the fixed catalyst bed.

The initial pressure of the reaction gas mixture input stream on entry thereof into the fixed catalyst bed in the process according to the invention will generally be from 1.5 to 6 bar, frequently from 2 to 5 bar and in many cases from 3 to 4 bar.

The temperature of the reaction gas mixture input stream on entry thereof into the fixed catalyst bed in the process according to the invention will generally be from 300 to 700° C., frequently from 350 to 600° C. and in many cases from 400 to 500° C.

In this document, the loading of a fixed catalyst bed catalyzing a reaction step with reaction gas shall be understood quite generally to mean the amount of reaction gas in standard liters (=1(STP); the volume in liters that the appropriate amount of reaction gas would take up under standard conditions (0° C., 1 atm)) which is conducted through one liter of fixed catalyst bed per hour. However, the loading may also be based only on one constituent of the reaction gas.

In that case, it is the amount of this constituent in 1(STP)/l·h which is conducted through one liter of the fixed catalyst bed per hour (pure inert material beds are not counted in a fixed catalyst bed). The loading may also be based only on the amount of catalyst present in a fixed catalyst bed which comprises the actual catalyst diluted with inert material (this is then noted explicitly).

In principle, the process according to the invention can be conducted at loadings on the fixed catalyst bed (based on the total amount of catalyst present therein), both with reaction gas and with the at least one hydrocarbon to be dehydrogenated which is present therein (e.g. propane), of from 100 to 10 000 $h^{-1}$(1(STP)/l·h, $h^{-1}$ for short), frequently from 300 to 5000 $h^{-1}$, i.e. in many cases from 500 to 3000 $h^{-1}$ (substantially irrespective of the desired conversion of the at least one hydrocarbon to be dehydrogenated).

In general, in the process according to the invention, the input gas stream I will flow essentially vertically toward the fixed catalyst bed disposed in the shaft. In other words, the angle β enclosed between the flow direction of the input gas stream I in the shaft and a plane aligned to the flow surface of the fixed catalyst bed is normally 90±30°, preferably 90±20°, more preferably 90±10°, even more preferably 90±5° and at best 90°.

Normally, the flow surface area of the fixed catalyst bed in the shaft in the process according to the invention is ≥1 $m^2$, in many cases also ≥2 $m^2$, or ≥3 $m^2$, or ≥4 $m^2$ or ≥5 $m^2$. Of course, the aforementioned flow surface area may also be ≥10 $m^2$, or ≥20 $m^2$, or ≥30 $m^2$. In world scale plants, the aforementioned flow surface area may also be ≥40 $m^2$ or ≥50 $m^2$. Corresponding flow surface areas of ≥100 $m^2$ are usually exceptional.

Useful catalysts for the catalytically active bed are in principle all dehydrogenation catalysts known in the prior art for heterogeneously catalyzed dehydrogenations. They can be divided roughly into two groups, specifically into those which are of oxidic nature (for example chromium oxide and/or aluminum oxide), and into those which consist of at least one generally comparatively noble metal (e.g. platinum) deposited on a generally oxidic support (for example zirconium dioxide, aluminum oxide, silicon dioxide, titanium dioxide, magnesium oxide, lanthanum oxide and/or cerium oxide). The dehydrogenation catalysts which may be used thus include those recommended in WO 01/96270, EP-A 731 077, DE-A 102 11 275, DE-A 101 31 297, WO 99/46039, U.S. Pat. No. 4,788,371, EP-A 705 136, WO 99/29420, U.S. Pat. Nos. 4,220,091, 5,430,220, 5,877,369, EP-A 117 146, DE-A 199 37 196, DE-A 199 37 105, U.S. Pat. Nos. 3,670,044, 6,566,573 and WO 94/29021. These catalysts in the process according to the invention may, for the reasons stated at the outset, be the sole catalysts in the catalytically active bed of the process according to the invention. In principle, the catalytically active bed may consist exclusively of catalytically active shaped bodies. Of course, the catalytically active bed may also consist of catalytically active shaped bodies diluted with inert shaped bodies. Such inert shaped bodies may be manufactured, for example, from fired clays (aluminum silicates) or steatite (e.g. C 220 from Ceram Tec), or other high-temperature ceramic materials (preferably substantially free of pores) such as aluminum oxides, silicon dioxide, titanium dioxide, magnesium oxide, lanthanum oxide, cerium oxide, zinc aluminum mixed oxide, thorium dioxide, zirconium dioxide, silicon carbide or other silicates such as magnesium silicate, and mixtures of the aforementioned materials. The aforementioned materials are also useful for the inert cover bed and, if appropriate, final bed of the fixed catalyst bed of the process according to the invention.

Advantageously, the inert cover bed of the fixed catalyst bed of the process according to the invention should be such that, in the reaction gas mixture input stream as it flows through this inert bed, ≤35 mol % (preferably ≤30 mol %, more preferably ≤25 mol %, better ≤20 mol %, particularly advantageously ≤15 mol %, even better ≤10 mol % and most preferably ≤5 mol % or 0 mol %) of the molecular oxygen present therein is converted.

In particular, the catalysts used as the (for example sole) catalysts for the catalytically active bed of the fixed catalyst bed for the process according to the invention may be those according to example 1, example 2, example 3 and example 4 of DE-A 199 37 107.

These are dehydrogenation catalysts which comprise from 10 to 99.9% by weight of zirconium dioxide, from 0 to 60% by weight of aluminum oxide, silicon dioxide and/or titanium dioxide, and from 0.1 to 10% by weight of at least one element of the first or second main group, of an element of the third transition group, of an element of the eighth transition group of the Periodic Table of the Elements, lanthanum and/or tin, with the proviso that the sum of the percentages by weight adds up to 100% by weight.

In a preferred embodiment, aforementioned dehydrogenation catalysts comprise at least one element of transition group VIII, at least one element of main group I and II, at least one element of main group III and/or IV and at least one element of transition group III including lanthanides and actinides. As element of transition group VIII, the active composition of the dehydrogenation catalysts comprises preferably platinum and/or palladium, more preferably platinum. As elements of main group I and II, the active composition of the aforementioned dehydrogenation catalysts comprises preferably potassium and/or cesium. As elements of transition group III including the lanthanides and actinides, the active composition of the aforementioned dehydrogenation catalysts comprises preferably lanthanum and/or cerium. As elements of main group III and/or IV, the active composition of the aforementioned dehydrogenation catalysts comprises preferably one or more elements from the group consisting of boron, gallium, silicon, germanium, tin and lead, more preferably tin. Most preferably, the active composition of the aforementioned dehydrogenation catalysts comprises in each case at least one representative of the aforementioned element groups.

Generally, the dehydrogenation catalysts may be catalyst extrudates (diameter typically from 0.1 or 1 to 10 mm, preferably from 1.5 to 5 mm; length typically from 1 to 20 mm, preferably from 3 to 10 mm), tablets (preferably the same dimensions as for the extrudates) and/or catalyst rings (external diameter and length typically from 2 to 30 mm or to 10 mm, wall thickness appropriately from 1 to 10 mm, or to 5 mm, or to 3 mm).

In principle, there are no restrictions either with regard to the catalyst geometry (especially in the case of supported catalysts) or with regard to the geometry of the inert shaped bodies. Particularly frequent geometries are solid cylinders, hollow cylinders (rings), spheres, cones, pyramids and cubes, and also extrudates, wagonwheels, stars and monoliths.

The longest dimension of the shaped catalyst bodies and of the inert shaped bodies (longest direct line connecting two points on the shaped body surface) may be from 0.5 mm to 100 mm, often from 1.5 mm to 80 mm, and in many cases from 3 mm to 50 mm or to 20 mm.

Finally, the catalysts of the German application No. 10 2005 044 916 should also be cited as (for example sole catalysts) particularly suitable catalysts for the catalytically active bed of the fixed catalyst bed of the process according to the invention.

In the context of the process according to the invention, high-boiling high molecular weight organic compounds up to and including carbon which are deposited on the catalyst surface and deactivate the catalysts can be removed and the catalyst can be regenerated by flowing the fixed catalyst bed through from time to time with a gas comprising oxygen at elevated temperature and thus effectively burning off the substances deposited.

After a prolonged operating time, the catalysts recommended in this document can normally be regenerated in a simple manner, for example, by first, in first regeneration stages, passing air (preferably) diluted with nitrogen and/or steam through the fixed catalyst bed at an entrance temperature of from 300 to 600° C. (in extreme cases if appropriate also up to 750° C.), frequently from 400 to 450° C. The catalyst loading with regeneration gas may (based on the total amount of catalyst regenerated), for example, be from 50 to 10 000 $h^{-1}$ and the oxygen content of the regeneration gas from 0.5 to 20% by volume.

In subsequent further regeneration stages, the regeneration gas used under otherwise identical regeneration conditions may be air. Appropriately from an application point of view, it is recommended to purge the catalyst with inert gas (e.g. $N_2$, for example industrial nitrogen with up to 1% by volume of $O_2$, $H_2O$ or mixtures thereof) before it is regenerated.

Subsequently, it is generally advisable also to regenerate with pure molecular hydrogen or with molecular hydrogen diluted by inert gas (preferably steam and/or nitrogen) (the hydrogen content should be ≥1% by volume) under otherwise identical conditions.

According to the invention, the ratio of the bed length X (in flow direction of the reaction gas mixture input stream) of the inert cover layer of the fixed catalyst bed and the distance d in the projection plane E, i.e. X:d, is ≥0.05, preferably ≥0.07 and particularly advantageously ≥0.1. Frequently, the aforementioned X:d ratio in the process according to the invention will be ≥0.2, or ≥0.3, or ≥0.5 or ≥1. Normally, the X:d ratio in the process according to the invention is, however, usually ≤10 and in many cases ≤5.

It is favorable for the process according to the invention when, on entry of the reaction gas mixture into the actual catalytically active bed of the fixed catalyst bed disposed beyond the inert bed in flow direction, the distribution of the molecular oxygen in the reaction gas mixture is highly homogeneous. The difference between the highest local volume concentration of molecular oxygen and the lowest local volume concentration of molecular oxygen in the reaction gas mixture should, based on the mean volume concentration of molecular oxygen in the reaction gas mixture, on entry of the reaction gas mixture into the actual catalytically active bed, preferably not be more than 200%, preferably not more than 150%, more preferably not more than 100% and most preferably not more than 50% or not more than 25%.

Typical induction times J in the process according to the invention may be ≤2000 ms, or ≤1000 ms, or ≤500 ms, or ≤100 ms, or ≤50 ms, or ≤20 ms, or ≤10 ms. Normally, the induction times J in the process according to the invention are, however, at values of ≥1 ms.

In principle, the gas lines of the line system conducting the input gas II in the process according to the invention may have any desired cross section. In other words, the cross section may, for example, be round (for example circular, or oval or elliptical) or polygonal (e.g. triagonal, tetragonal or hexagonal, etc.).

Appropriately from an application point of view, the cross section of the lines conducting the input gas II where the exit orifices A are disposed is polygonal, preferably triagonal or tetragonal. The cross section of the lines (channels) conducting the input gas II in the process according to the invention where the exit orifices A are disposed is preferably square or rectangular (in that case, the exit orifices A are as close as possible to the closest corner of the tetragon to the fixed catalyst bed). The cause to which the above is attributable is that, when the aforementioned polygonal cross sections are employed, both the distances D and the angles α for all exit orifices A can be manufactured (adjusted) uniformly both in a more precise manner and more easily. The exit orifices A themselves are, even in the case of the aforementioned angular cross sections, preferably round (circular) and are preferably manufactured with uniform diameter over all exit orifices A. Preferably in accordance with the invention, D is identical for all exit orifices A. Advantageously in accordance with the invention, α for all exit orifices A is additionally also identical and is advantageously 90°±5° or 90°. Moreover, the input gas II streams exiting from the exit orifices A are advantageously also identical in the process according to the invention and the exit orifices A, with regard to the flow surface of the fixed catalyst bed with the reaction gas mixture input stream, are preferably ideally distributed uniformly over the flow surface.

When the fixed catalyst bed in the process according to the invention, in a shaft reactor configured as a tray reactor, is the next fixed catalyst bed in flow direction of the reaction gas downstream of another fixed catalyst bed (precursor fixed catalyst bed), it is advantageous for the process according to the invention when the precursor fixed catalyst bed is (charged) in a highly uniform, highly homogeneous manner (especially regarding the bed length in flow direction of the reaction gas).

The consequence of such a highly uniform configuration of the precursor fixed catalyst bed is substantially uniform flow as the reaction gas passes through the precursor fixed catalyst bed and, resulting from this, a very substantially uniform pressure level over the input gas stream I of the process according to the invention.

In this way, it is possible to achieve what is generally advantageous for the process according to the invention, specifically that the maximum pressure difference occurring among the local pressures existing in the input gas stream I upstream of the exit orifices A is smaller than or at most just as great as the pressure drops occurring as the individual input gas II streams exit from the exit orifices A. When the latter pressure drops are, for example, 5 mbar, it is advantageous in accordance with the invention when the aforementioned maximum pressure difference occurring is not more than 3 mbar.

It should also be emphasized at this point that the line system conducting the input gas II in the process according to the invention is advantageously configured such that the pressure drop is very low on the way from the injection point of the input gas II into the line system up to the arrival of the input gas II at the exit orifices A (especially relative to the pressure drop as it passes through the exit orifices A; in general, it should not be more than one fifth, advantageously not more than one tenth of the aforementioned pressure drop), and highly uniform in the case of uniform exit orifices A (especially when the input gas II is fed controlled to a certain total feed rate). Such low pressure drops are attained, for example, when the length of the line system and the flow rate in the line system are very low and the flow cross section in the line system is kept large.

When the process according to the invention is employed in a tray reactor with a plurality of fixed catalyst beds (if appropriate with all (or all but one) disposed in the tray reactor), input gas II is fed upstream of each fixed catalyst bed, preferably with an independent line system. In principle, these independent line systems can, however, all be supplied (fed) from one input gas II source.

In general, they will be, however, fed with different input gases II (having a different composition).

Useful material for the manufacture of the equipment required for the process according to the invention is in particular the steels recommended in the German application No. 10 2005 061 626, especially also stainless steel of DIN type 1.4841 on the side in contact with the product.

The process according to the invention is advantageous especially when it is performed in a shaft reactor configured as a tray reactor and all fixed catalyst beds disposed in the shaft reactor are employed, if appropriate excluding the first fixed catalyst bed in the shaft reactor in flow direction of the reaction gas. The latter exception will generally be made when the reaction gas fed to the shaft reactor already comprises the at least one hydrocarbon to be dehydrogenated, if appropriate a sufficient amount of molecular hydrogen and, in accordance with the requirement, molecular oxygen. The latter is normally the case when the reaction gas fed to the shaft reactor configured as a tray reactor comprises residual gas which stems from a partial oxidation, connected downstream (and generally likewise heterogeneously catalyzed) of the heterogeneously catalyzed partial dehydrogenation of the at least one hydrocarbon to be dehydrogenated (e.g. propane) to at least one dehydrogenated hydrocarbon (e.g. propylene), of the at least one dehydrogenated hydrocarbon (e.g. propylene to acrolein and/or acrylic acid as the target product) accompanied by remaining hydrocarbon (still) to be dehydrogenated, and comprises oxygenate (e.g. unconverted molecular oxygen) remaining after target product removal from the product gas mixture of the partial oxidation (a full oxidation (combustion) of a dehydrogenated hydrocarbon and/or hydrocarbon to be dehydrogenated is understood in this document to mean that the entire amount of carbon present in the hydrocarbon is converted to oxides of carbon ($CO$, $CO_2$) and the hydrogen present thereinto $H_2O$; all different reactions of a dehydrogenated hydrocarbon and/or of a hydrocarbon to be dehydrogenated with the reactive action of molecular oxygen are encompassed in this document with the term "partial oxidation"; the additional reactive action of ammonia indicates ammoxidation, which is likewise to be encompassed under the term "partial oxidation").

For example, the reaction gas fed to the shaft reactor may be a mixture of fresh hydrocarbon to be dehydrogenated (e.g. fresh propane) and aforementioned residual gas (which generally also comprises steam) (if appropriate, $H_2$, $H_2O$ and/or $O_2$ may, though, additionally be metered into the reaction gas before it enters the shaft reactor configured as a tray reactor; for example, dehydrogenation cycle gas according to WO 03/076370 or according to DE-A 102 11 275 can also be metered into the reaction gas before it enters the tray reactor.

The design of such a shaft reactor configured as a tray reactor (cf. FIGS. 1 and 2) may (as is quite generally the case for the process according to the invention) be configured as follows (the numerical addresses used below relate to FIGS. 1 to 17 of this application; the dimensions specified relate in the context, by way of example, to a specific embodiment of such a reactor; of course, corresponding axial tray reactors may also be designed larger or smaller; the number of fixed catalyst beds may also be increased or lower).

The axial tray reactor detailed by way of example below is delimited externally (i.e. from the environment) by the shell (1) of a straight circular cylinder (when the end points of parallel radii of two equally large circles lying in parallel planes are joined to one another by lines which are at right angles to the two parallel circular planes (base surface and top surface (the first of the two circle surfaces in flow direction of the reaction gas), what is formed is a straight (undeviating) circular cylinder (also known as rotational cylinder; the line connecting the circle centers is known as axis of the circular cylinder)) which is concluded both at the top and at the bottom by a curved hood (2, 3) having a semiellipsoidal shape (to DIN 28011) (shell and hoods together form the pressure vessel shelf). Below the lower semiellipsoidal base, the pressure vessel is enclosed by a support frame which is in turn borne, for example, by from four to eight supports. The shell thickness is 30 mm. The outer diameter of the circular cylindrical shell is 6070 mm. The separation of base surface and top surface of the circular cylinder is 2640 mm. The height both of the upper and of the lower hood is 1350 mm (in each case determined from the center of the circular base surface or top surface to the particular hood maximum). The wall thickness of the upper hood (3) is a uniform 30 mm; the wall thickness of the lower hood (2) begins at 30 mm and thickens toward the gas outlet tube stub constantly to 45 mm.

The upper hood tapers off in a centered (central) gas inlet tube stub (4). Its internal diameter is 1200 mm. The lower hood tapers off in a corresponding manner in a centered (central) gas outlet tube stub (5). Its internal diameter is 1400 mm. The stub height is in each case 240 mm (when appropriate insulating materials are applied to the outside of the pressure vessel wall for thermal insulation (for example in a layer thickness of from 300 to 500 mm), the stub height is correspondingly greater, since the stub should, appropriately in accordance with the application, project out of the insulating layer). Where the lower hood tapers off into the gas outlet tube stub (5), the hood is additionally equipped with a reinforcement ring (6) which is welded on at the hood and at the stub. Its external diameter is 1900 mm and its thickness is 50 mm. While the lower reactor hood is joined to the circular cylindrical shell, preferably by welding-on, the upper reactor hood is joined to the circular cylindrical shell preferably by a flange connection (7) (between a peripheral flange of the circular cylindrical shell (8) and a corresponding peripheral flange on the hood (9)) with weld lip sealing (10). FIG. 5 shows an enlarged detail of the flange connection in longitudinal section including weld lip seal (10) (the latter is typically manufactured from steel sheets which have a thickness of approx. 2 mm; corresponding weld lip seals are also shown by WO 2004/067164). The gas leakage through the flange connection used should be $<10^{-4}$ mbar·l/s. The removability of the upper hood eases the filling with and the withdrawal of inert shaped bodies and/or catalysts, for example in the case of a partial catalyst change or in the case of a full catalyst change.

In order to minimize the residence time of a reaction gas which has been added via the gas inlet tube stub (4) and comprises the at least one hydrocarbon to be dehydrogenated and molecular oxygen in the interior of the upper reactor hood (3) (and thus to very substantially prevent undesired side reactions in a reaction gas already having elevated temperature), the inner volume of the hood is reduced by means of an inserted intermediate ceiling (11) whose shape can correspond, for example, to the shell (with a shell thickness of 15 mm) of a straight circular frustocone or two straight frustocones placed one on top of the other.

The inner wall of the upper hood and the shells of the circular frustocones are appropriately reinforced with radially arranged ribs (cf. WO 2004/067164).

The circle covered by the circular frustocone corresponds to the base circle of the gas inlet tube stub (4). Of course, the intermediate ceiling may also be curved outward toward the top surface of the circular cylinder of the shell, as shown, for example, in FIG. 5 and in FIG. 7 and in FIG. 9 of WO 2004/067164. The inserted intermediate ceiling (11) should preferably reduce the inner volume of the hood available to the reaction gas, based on its value in the absence of an intermediate ceiling, by at least 50% by volume, but normally by not more than 90% by volume. The intermediate ceiling (11) is mounted by welding-on. Appropriately from an application point of view, the intermediate ceiling itself has, distributed essentially uniformly on its circumference, from 3 to 36 passage orifices whose orifice cross section is from 1 to 8 $cm^2$. The space R enclosed between intermediate ceiling and reactor hood communicates with the remaining inner volume of the hood through these passage orifices. In order to ensure that essentially no reaction gas penetrates through aforementioned passage orifices into the space R, the space R is purged continuously with an inert gas (preferably molecular nitrogen, for example industrial nitrogen with up to 1% by volume of $O_2$, steam or mixtures thereof) which is supplied into the hood lid through from 1 to 12 feed lines (53) and removed through the passage orifices (added to the reaction gas). This inert gas stream will generally be, in total, less than 1% by volume, usually even less than 0.1 or less than 0.01% by volume, based on the volume flow rate of the reaction gas (in $m^3$ (STP)).

The pipeline supplying the reaction gas is connected in a gas-tight manner to the gas inlet tube stub (4), likewise by flange attachment, as is the pipeline removing the product gas stream to the gas outlet tube stub (5). Appropriately from an application point of view, a weld lip seal is employed in both cases. Alternatively, the feeding pipeline can also be welded directly onto the gas inlet tube stub (4).

For proper and safe operation, the aforementioned (pipe) lines are preferably equipped with devices for compensating for longitudinal expansion effects, as can occur, for example, owing to temperature changes, compensators which feature a lateral mode of action being used advantageously.

These compensators generally having a multilayer design may be manufactured from the same material as the pipeline itself. However, particularly advantageous embodiments are those with (generally: gas-permeable rigid inner tube and gas-impermeable elastic outer shell (gas-impermeable elastic outer tube)) an inner tube part which is in contact with the gas to be conducted, is manufactured preferably from stainless steel of DIN materials number 1.4893, and appropriately has a gas-permeable expansion joint and an external, gas-impermeable, elastic, corrugated part which is manufactured at least partly from an especially mechanically and thermally stressable material, for example the material 1.4876 (designation according to VdTÜV-Wb 434) or 1.4958/1.4959 (designation according to DIN 17459) or INCOLOY 800 H or 800 HT, or nickel-base material 2.4816 (alternative designation Alloy 600) or 2.4851 (alternative designation Alloy 601).

Otherwise, all parts of the tray reactor in question may be manufactured from the stainless steel of DIN materials number 1.4893 or from another stainless steel recommended or mentioned in the German application 10 2005 061 626, in particular also from stainless steel of DIN type 1.4841 on the side in contact with the product.

The interior of the lower hood is divided by the attachment of twelve lamellae (walls) (12) on the inner wall of the hood over the entire hood height into twelve (possible alternatives are also eight, six, or four, or three, or sixteen) congruent sectors (chambers). On the side in contact with the inner wall of the hood, the shape of the individual lamella (of the particular lamella ridges) is adapted to the hood curvature. The wall thickness of the lamellae is uniform 30 mm. In addition to the lamella ridge, the individual attached lamellae each have two edges K and C. The edges K run parallel to the axis of the circular cylinder of the shell and extend with a length of 1400 mm from the inner wall of the lower hood up to the base surface of the circular cylinder of the shell, on which the edges K stand at right angles. The edges K form the face of the particular lamellae facing the hood interior. The edges C are in contact with the base surface of the circular cylinder of the shell and conclude the individual lamella at the top. Like the aforementioned base surface itself, they enclose a right angle with the corresponding edge K, i.e. they run on a radius of this circular base surface. While these radii, however, have a length of 3010 mm, the length of the edges C is only 2460 mm. The edge C does not protrude at the edge K, but rather concludes flush where it collides with the edge K. This means that the edges K of opposite lamellae (their edges C lie on the same diameter of the base surface of the circular cylinder of the shell) are not in contact, but rather have a separation of in each case 1100 mm.

The edges K end at their lower end on the outline of the gas outlet tube stub.

When the lamellae edges C of two adjacent lamellae are extended to such an extent that they intersect, these lamellae edges each enclose an angle of 30°. Two adjacent lamellae thus, together with the inner hood wall to which they are attached, each enclose a chamber which is open both toward the base surface of the circular cylinder of the shell and toward the central axis of the lower hood (=downward extension of the axis of symmetry of the circular cylinder of the shell). In addition, the lamella walls may have passage orifices through which adjacent chambers can additionally communicate with one another. Since the twelve lamellae rest on the inner wall of the lower hood only by virtue of gravity and are not joined to the inner wall of the lower hood by means of a weld seam, the positioning and the relative arrangement of the twelve lamellae is stabilized with the aid of struts (13) mounted (welded on) in each case between two adjacent lamellae.

Where the base surface of the circular cylinder of the shell and the lower hood meet is mounted (welded onto the inner wall of the hood) a bearing ring (14) which runs horizontally and has a bearing width of 60 mm. The thickness (height) of the bearing ring is 20 mm.

Where the individual lamellae meet the bearing ring at the bottom, they have a precisely fitting notch into which the bearing ring is inserted seamlessly, so that the edge C and the bearing surface of the bearing ring are on one level and the bearing surface supplements the edge C to its length in the absence of the notch.

To accommodate the various fixed catalyst beds in the above-described pressure vessel, an appropriate number of circular ring cylinder units is inserted into it.

A circular ring is understood to mean the area in one plane which is delimited by two concentric circular rings with different radius. When, in two congruent (coincident) circular rings (the base circular ring and the top circular ring) lying in parallel planes, the particular end points of parallel radii on the two outer circles and the particular end points of parallel radii on the two inner circles are connected by lines, this forms a circular ring cylinder. The connecting lines of the end points on the two inner circles are called inner shell lines of the circular ring cylinder (its entirety forms an inner shell) and the connecting lines of the end points on the two outer circles are called outer shell lines of the circular ring cylinder (their entirety forms an outer shell). When the shell lines are vertical on the two circular rings, the circular ring cylinder is straight or undeviating. The connecting line of the circular ring centers is called axis of the circular ring cylinder. When a straight circular ring cylinder is intersected by two planes which are parallel to the base circular ring and top circular ring and have the distance H from one another, a circular ring cylinder unit of height H is formed between the planes, which likewise has a base circular ring and a top circular ring.

The wall thickness of the outer shell of the circular ring cylinder units used for the pressure vessel described is 20 mm and the wall thickness of the inner shell of the circular ring cylinder units used for the pressure vessel described is 30 mm. Their height H is 850 mm (exception: the height H is 710 mm for the first circular ring cylinder unit in flow direction of the reaction gas). The radius of the inner circle of the aforementioned circular cylinder units (distance from the circular ring center to the inner shell of the circular ring cylinder units) is 600 mm; the radius of the outer circle of the aforementioned circular ring cylinder units (distance from circular ring center to the outer shell of the circular ring cylinder units) is 2900 mm. The distance between the outer shell of the circular ring cylinder units and the inner shell of the circular ring cylinder units is thus 2270 mm.

The space enclosed by the inner shell is referred to as the circular ring cylinder unit interior. The space present between the outer and the inner shell is referred to as circular ring cylinder unit interstice.

Twelve dividing walls $W_T$(15) which have a wall thickness of 30 mm divide the circular ring cylinder unit interstice into twelve congruent sector spaces.

The individual dividing wall has a height H corresponding to the unit height H. The length T of a dividing wall corresponds to the distance between the outer shell of the circular ring cylinder unit and the inner shell of the circular ring cylinder unit. In accordance with these facts, the individual dividing wall is welded on both at the outer shell and at the inner shell over its height H. The height H of the dividing wall is at right angles to the base circular ring and top circular ring of the circular ring cylinder unit. The length T of the dividing wall runs radially from the outer to the inner shell and ends, when it is extended theoretically, in the axis of the circular ring cylinder unit. When two adjacent dividing walls are extended in the manner described above until they intersect, they enclose an angle of 30°.

When a first circular ring cylinder unit segmented as described is inserted into the pressure vessel described, it is placed in a simple manner on the bearing ring (14), and in such a way that, firstly, there is a distance of 50 mm between the circular cylinder of the shell of the pressure vessel and the outer shell of the circulating cylinder unit, and, secondly, the dividing walls of the circular ring cylinder unit and the lamella walls rest on one another (or above one another, i.e. coincidently) in the lower hood of the pressure vessel (i.e. the axis of the circular cylinder of the shell and the axis of the circular ring cylinder unit coincide). The base circular ring is present beyond the top circular ring of the inserted segmented circular ring cylinder unit in flow direction of the reaction gas.

Between adjacent walls $W_T$ are inserted in each case ten uncurved transverse walls (bearing walls) Q (54) as a bearing structure, which have a height of 200 mm and a wall thickness of 20 mm, The bearing walls are attached to the walls $W_T$ by welding. The length of the bearing walls increases naturally with increasing distance thereof from the inner shell of the circular ring cylinder unit or with decreasing distance from the outer shell of the circular ring cylinder unit.

With respect to one another, the bearing walls Q within one and the same sector space are, appropriately from an application point of view, arranged equidistantly.

The bearing walls Q are inserted such that the distance of their lower edge from the base circular ring of the segmented circular ring cylinder unit is 40 mm.

In addition, the transverse walls Q have passage orifices O whose center is appropriately at half the height of the transverse wall. With increasing distance from the inner shell of the circular ring cylinder unit, the number of passage orifices O per transverse wall increases. Transverse walls disposed in different sector spaces, which have the same distance from the inner shell of the circular ring cylinder unit, are appropriately configured so as to be congruent. The passage orifices Q are preferably circular.

A grid sector which bears the fixed catalyst bed is placed in a precisely fitting manner onto the bearing structure thus created within a sector space.

In general, the shaped catalyst bodies are not poured directly onto the grid sector (if appropriate, a network of metal mesh (for example made of the stainless steel from which the pressure vessel is manufactured) with small mesh size is applied to the grid). This is because the shaped catalyst bodies typically have a smaller dimension than the mesh size of the grid. In the reactor described, the mesh size of the grid sectors used is appropriately from 2 or 3 to 7 mm, for example 4 mm.

Correspondingly, inert spheres of C 220 steatite from CeramTec with a diameter of 5 mm are first poured on in a bed height of 50 mm uniform over all grid sectors, which is followed by a bed of shaped catalyst bodies. A further inert bed of bed height 25 mm of spheres of the same steatite, but with a diameter of from 2 to 3 mm, is poured onto this inert bed, and is followed by a bed of shaped catalyst bodies. The shaped catalyst bodies used are, for example, extrudates of diameter 1.5 mm and a length in a Gaussian distribution in the range from 10 mm to 15 mm with a maximum at approx. 12.5 mm (elemental stoichiometry (mass ratio of the active elements including support) and catalyst precursor preparation and activation to the active catalyst are otherwise as described in Example 4 of DE-A 102 19 879).

The bed height of the shaped catalyst bodies is a uniform 300 mm (its uniformity can be achieved in a simple manner, for example, by placing a perforated plate or a mesh onto the completed bed (onto the top circular ring) and removing shaped catalyst bodies which project through its orifices). Subsequently, the fixed catalyst bed is concluded with a bed of rings of C 220 steatite from CeramTec (up to the top circular ring of the segmented circular ring cylinder unit). The geometry of the steatite rings is 7 mm×7 mm×4 mm (external diameter×height×internal diameter) and the bed height is a uniform 200 mm (exception: this bed height is only 60 mm in the first circular ring cylinder unit in flow direction of the reaction gas).

Uniform bed heights of the inert beds can be achieved, for example, in a simple manner by placing a pouring aid (16) according to FIG. 6, which remains in the inert bed, onto each grid sector, which has a height corresponding to the bed height, so that it is possible to smooth off the inert bed to a uniform bed height in a simple manner along it. The wall thickness of its elements is typically from 0.3 to 2 cm. Appropriate pouring aids can also be used in the bed of active bodies.

Alternatively to the steatite rings, it is also possible to use 7 mm×7 mm solid steatite cylinders (external diameter× height). As a further alternative, it is also possible to use steatite spheres having a diameter of from 5 mm to 6 mm.

Two further such circular ring cylinder units charged with such a fixed catalyst bed are placed onto this last (lowermost) circular ring cylinder unit charged with a fixed catalyst bed in flow direction. The dividing walls $W_T$ of all circular ring cylinder units are coincident, i.e. on one another in the same manner as their outer and inner shells.

Where the circular ring cylinder units rest on one another, there are unavoidably slight, gas-permeable joins. The space (gap) between the circular cylinder shell (1) of the pressure vessel and the outer shells of the circular ring cylinder units charged with fixed catalyst bed is appropriately filled with thermal insulating material (for example mineral wool or glass wool) which rests on the bearing ring (14).

At the height of the top circular ring of the particular circular ring cylinder unit, the circular cylinder shell (1) of the pressure vessel and the outer shell of the circular ring cylinder unit charged with fixed catalyst bed are each bonded to one another in a gas-impermeable manner by means of a weld lip seal (17). FIG. 7 shows an enlargement of the weld lip seal (17) in longitudinal section. It is constructed so as to be capable of absorbing thermal contractions and expansions (both in dehydrogenating operation and in the course of catalyst regeneration, significant temperature changes occur) of the particular circular ring cylinder unit without breaking up and losing the seal. At the height of the base circular ring of the particular circular ring cylinder unit, there is no corresponding seal, which is why reaction gas passes from there in each case into the space (gap) between circular cylinder (1) of the pressure vessel and the outer shell (18) of the particular circular ring cylinder unit and accomplishes pressure equalization.

Below the top circular ring of the lowermost (last) circular ring cylinder unit in flow direction of the reaction gas, but above the base circular ring of the same circular ring cylinder unit, a base (19) which extends over the entire circular cross section of this interior and is correspondingly configured in a circular shape is welded in a gas-tight manner onto the inner shell of this circular ring cylinder unit in the circular ring cylinder unit interior. Where two circular ring cylinders rest on one another, a metal sheet (top band) which runs around the circumference of the circular ring cylinder unit interior and, below the weld seam, projects flush over the joint existing between the circular ring cylinder units resting on one another is welded on above the base circular ring of the upper circular ring cylinder unit from flow direction of the reaction gas in the accompanying circular cylinder unit interior on the inner shell. The top band is about 8 mm thick and 60 mm wide.

Otherwise, the three circular ring cylinder unit interiors arranged one on top of the other together form an undeviating circular cylindrical overall interior (20) which is completed at the bottom by the base (19) and opens at the top into the upper hood.

The tubes (21) through which the input gas II required for the process according to the invention flows (input gas II feed tubes) are conducted within this overall interior (20). The residual space in the overall interior (20) remaining around the input gas II feed tubes is filled with quartz sand which has a particle size of from 0.3 to 1.2 mm (alternatively, it is also possible to use oxide ceramic spall, granules and/or spheres (or other finely divided shaped bodies); the filling is preferably dust-free, which can be brought about, for example, by washing it with water and subsequent drying (for example fire drying)). The filling ends just (approx. 1 cm) below the top circular ring of the first circular ring cylinder unit in flow direction of the reaction gas. A metered addition of input gas II is undertaken between the first and the second and between the second and third fixed catalyst bed (in flow direction of the reaction gas).

The access (22) of the tubes (21) into the reactor is via the upper reactor hood (3) through entrance ports (23) disposed therein and welded to it in a fixed manner.

The external tube diameter is 168.3 mm and the wall thickness may be from 2 to 7 mm. In each case three such tubes (input gas II feed tubes) provide the supply with input gas II between two aforementioned fixed catalyst beds. Within one such group of three input gas II feed tubes, the feeding with input gas II is from one and the same source. In general, however, the composition of the input gas II which is fed between the first and the second fixed catalyst bed (in flow direction) and the composition of the input gas II which is fed between the second and the third fixed catalyst bed will be different from one another and stem from different sources.

The metering of input gas II to the particular group of three input gas II feed tubes is effected in each case with control of total amounts.

The sealing of the entrances of the input gas II feed tubes into the upper reactor hood is shown by FIG. 8 in longitudinal section. The sealing is effected by means of an outer and an inner flange bond. The transition of a tube conducting input gas II into the entrance port (23) is in three pieces (three-piece). These three parts are the tube section in the entrance port (24), the tube section outside the entrance port (25) and the tube section in the intermediate plate (26). The inner flange bond binds the lower tube section from below in a gas-tight manner to the tube section in the intermediate plate and the outer flange bond firstly seals the entrance port from the environment and simultaneously binds the upper tube section in a gas-tight manner from above to the tube section in the intermediate plate. The sealing materials used may be materials based on, for example, mica or combed graphite or metallic sealants. The above-described construction method enables, as early as after release of the outer flange bond, the raising of the upper reactor hood without having to change the position of the tubes (21).

An alternative seal of the entrances of the input gas II feed tubes into the upper reactor hood is shown by FIG. 9 in longitudinal section.

The transition of a tube conducting input gas II into the entrance port (23) is in two pieces. These two pieces are the tube section in the entrance port (27) and the tube section outside the entrance port (28). The internal diameter of the latter is from 10 to 30 mm greater than the internal diameter of the former. The gas-tight transition between the two is by means of a flange bond. To this end, a peripheral flange is welded on at the upper end of the port and projects up to the tube section conducted within the port which protrudes from 10 to 30 mm above this flange and is secured to the flange by means of a weld lip seal (29). At the lower end of the tube section outside the entrance port (28), a peripheral flange is likewise welded on. The sealing materials between the two flanges may be materials based on, for example, mica, combed graphite or a metallic sealant.

At the level of the passage orifices O of the transverse walls Q of the first circular ring cylinder unit in flow direction of the reaction gas and at the level of the passage orifices O of the transverse walls Q of the second circular ring cylinder unit in flow direction of the reaction gas are disposed, in the inner shell of the particular circular ring cylinder unit, in each case three passage orifices MO whose centers are on the corners of an equilateral triangle. The in each case three input gas II feed tubes deviate through these orifices MO (they are welded in a gas-tight manner into these orifices) and are conducted through passage orifices O of the transverse walls Q radially in the direction of the outer shell of the particular circular ring cylinder unit until they meet a circular input gas II distribution duct KR (30) mounted in the particular circular ring cylinder unit, to which they are welded and which has the same outer and inner tubular diameter as the input gas II feed tubes fed to it. The circular distribution duct KR is, at the level of the passage orifices O of the particular circular ring cylinder unit, conducted into the particular walls $W_T$ through viaduct-like passage orifices, but not welded onto the viaduct bridges.

The width of the gap between distribution duct KR and passage orifice is from about 4 to 15 mm.

The length of the input gas II feed tubes, calculated from their entrance into the upper reactor hood up to the particular circular distribution duct KR, is ≥3 and ≤6 m. The outer diameter of the circle drawn by the two circular distribution ducts is 2860 mm. The corresponding internal diameter is 2560 mm.

While the passage of the input gas II feed tubes through the passage orifices MO is sealed, this does not apply to the corresponding passages through the passage orifices O. Instead, these passages are communicating.

The gap width is from about 2 to 10 mm.

From the circular distribution duct KR (30), input gas II distribution tubes conducted through passage orifices O lead radially in the direction of the outer and in the direction of the inner shell of the corresponding circular ring cylinder unit.

The outer diameter of the distribution tubes is in the range from 80 to 110 mm and may, for example, be 88.9 mm. The wall thickness of the distribution tubes is in the range from 2.1 to 6.3 mm.

Between the transverse walls Q of the circular ring cylinder unit, the distribution tubes (32) deviate downward in the direction of the base circular ring of the circular ring cylinder unit.

Immediately below the bearing structure of the first circular ring cylinder unit in flow direction of the reaction gas and of the second circular ring cylinder unit in flow direction of the reaction gas (but not below the bearing structure of the third circular ring cylinder unit in flow direction of the reaction gas) are disposed cuboidal metering boxes (31) having exit orifices A and having the edges a, b and c and three pairs of congruent right angles as their delimiting surfaces, into which the distribution tubes according to the longitudinal section shown in FIG. 10 open (the wall thicknesses of the metering boxes are appropriately from 1 to 3 mm, preferably from 1.5 to 2.5 and advantageously 2 mm). Generally only one distribution tube opens into metering boxes (distribution boxes) with short edges a. Up to three distribution tubes open into metering boxes (distribution boxes) with a long edge a. The length of the edges c for all metering boxes is a uniform 40 mm and the length of the edges b for all metering boxes is a uniform 150 mm. In contrast, the lengths of the edges a vary for different boxes. One of the two pairs of congruent rectangles a×b for all boxes is in each case in the plane of the base circular ring of the circular ring cylinder unit.

The edges c are all at right angles to the plane of the base circular ring and point in the direction of the top circular ring belonging to the circular ring cylinder unit. The edges a of all boxes are aligned in parallel. The separation of two adjacent metering boxes is 130 mm. In this separation sequence, the metering boxes are arranged distributed over the entire cross section of the circular cylinder unit interior. The edges a run like secants from one side of the outer shell of the circular ring cylinder unit to the other side of this outer shell. When they meet the inner shell of the circular ring cylinder unit, the metering box is concluded just before the inner shell and continued on the opposite peripheral side of the inner shell as a (separate) new (fresh) metering box with corresponding edge length a. On the inner surface of the outer shell and on the outer surface of the inner shell of the circular ring cylinder unit are disposed mounts (33) (preferably configured so as to be positively locking), to which the metering boxes are secured in the middle of the rectangular surface b×c. FIGS. 11 (side view) and 12 (top view) show an example of such a mount configured so as to be positively locking.

In the case of use of metering polygons (preferably regular 12-sided) which are gas permeable over the entire angle range of 360° C., useful examples also include the following dimensions:

long edge b: 160 mm;

long edge c: 40 mm;

wall thickness of the metering boxes: 2 mm;

separation of radially successive metering boxes (internal width): 125 mm;

internal diameter of the exit orifices A: 2.5 mm;

separation of two exit orifices A adjacent on the string of beads (center to center): a uniform 60 mm;

separation of the theoretical string from the edge a which faces the base circular ring of the circular ring cylinder unit: 10 mm; and the exit orifices A of mutually radially opposite rectangular surfaces a×c of radially successive distributor boxes are opposite one another with a gap in between.

Appropriately in accordance with the application, the metering polygons are supplied with the input gas comprising molecular oxygen such that the metering points are distributed uniformly over the circumference of the polygon for one and the same polygon. The number of these metering points for one and the same polygon may, for example, be 2, or 3, or 4, or 5, or 6, or 7, or more. With increasing number of metering points, the pressure on the individual exit orifices A of the polygon becomes uniform. FIG. 18 shows a schematic of such a metering polygon structure.

In an alternative embodiment, the metering boxes may be arranged over the cross section of the circular ring cylinder unit interior, instead of in a secant-like manner, also in a spider's web-like manner as concentric polygons or as concentric circles. The individual polygons or circles may be manufactured throughout the entire angle range of 360° (a metering polygon or circle), or divided into separate metering boxes.

The arrangement of the metering boxes is appropriately undertaken coincidently (congruently) in both circular ring cylinder units.

The exit orifices A are disposed in the rectangular surfaces A×c of the cuboidal metering boxes (distribution boxes). They are all circular and have an internal diameter in the range from 2 to 4 mm, advantageously of 3 mm.

The exit orifices A are disposed in the two congruent rectangular surfaces a×c of a metering box (distribution box) like a successive row of beads on a string, the string having a separation of 5 mm from the edge a which faces the base circular ring of the circular ring cylinder unit and forming a parallel to this edge a. The distance from one exit orifice A to the next exit orifice A on the "string of beads" is (measured from center to center) always 100 mm (alternatively, it is also possible to use another uniform distance in the range from 50 to 100 mm). The total number of exit orifices A of all metering boxes (distribution boxes) mounted in one circular ring cylinder unit in the reactor described is about 2000 (when the separation of two adjacent exit orifices A on the string of beads is selected at <100 mm, the total number of exit orifices A may even be up to 10 000 or up to 5000). The edges a facing the base circular ring of the circular ring cylinder unit must not project from the base circular ring. Finally, it should also be emphasized that where the metering boxes (distribution boxes) meet dividing walls $W_T$, these dividing walls $W_T$ have corresponding passages for the metering boxes (distribution boxes), a gas-permeable gap of about 1 cm existing between the inner circumference of the passage orifice and the outer circumference of the metering box (distribution box). The exit orifices A of opposite rectangular surfaces a×c of adjacent rectangular boxes have gaps opposite one another.

In principle, the total number of exit orifices A, as described, may be identical in the different circular ring cylinder units.

They may also be different from one another. In other words, this total number may be increasing or decreasing from circular ring cylinder unit to circular ring cylinder unit in flow direction of the reaction gas.

The monitoring and control of an inventive heterogeneously catalyzed partial dehydrogenation of at least one hydrocarbon to be dehydrogenated in the axial tray reactor described is appropriately effected by means of the measurement of the temperatures present in the different catalytically active beds of the particular fixed catalyst bed.

The catalytically active bed of shaped catalyst bodies, within a fixed catalyst bed of the above-described axial tray reactor, has a bed height of 300 mm (30 cm) in flow direction of the reaction gas (of course, the tray reactor may, in a completely corresponding manner, also be designed for bed heights deviating from 30 cm (e.g. 40 cm); 40 cm-high bed heights are advisable, for example, when the shaped catalyst bodies used are corresponding catalyst strands of diameter 3 mm, which cause a lower pressure drop; the greater bed height advantageously entails a reduction in the diameter of the circular ring cylinder unit interior to 5.47 m and an associated catalyst bed outflow area of only 21.6 $m^2$).

In flow direction of the reaction gas, temperature measurements are effected at the following bed heights Sh of a catalytically active bed:

0 cm;
7.5 cm;
15 cm;
22.5 cm; and
30 cm.

When the bed height of the bed of the shaped catalyst bodies has a value different from 300 mm (for example 240 mm, or 260 mm, or 280 mm), the temperature measurements are effected at five heights distributed equidistantly in a corresponding manner over this bed height.

For this purpose, three guide fingers (34) for accommodating a triple thermoelement (the triple thermoelement simultaneously detects the temperature at three different (generally equidistant) insertion depths into the fixed catalyst bed) are conducted into the catalytically active bed at right angles to the axis of the corresponding circular ring cylinder unit (i.e. radially and horizontally) through the shell (1) of the straight circular cylinder and through the outer shell of the circular ring cylinder unit at each of the aforementioned heights Sh (cf. FIG. 13). The individual guide finger projects up to the inner shell of the circular ring cylinder unit and is sealed from the fixed catalyst bed. In other words, the interior of the particular guide finger does not come into contact with reaction gas. The internal diameter of a guide finger is in the range from 3 to 5 mm and the external diameter of a guide finger is in the range from 6 to 8 mm. The three guide fingers (34) installed at one and the same bed height Sh are distributed on the circumference of the shell (1) such that successive guide fingers along the circumference enclose an angle of 120° when they are theoretically extended until they intersect. In the case of guide fingers disposed in successive bed heights Sh, the next three guide fingers in flow direction are not coincident with the preceding three guide fingers, but rather are offset by 90°. The sense of the aforementioned offset (clockwise or counterclockwise) is retained over the catalytically active bed, so that the guide fingers coincide at Sh=0 cm and at Sh=30 cm, as shown in FIG. 14.

The temperatures determined at the bed heights Sh=0 cm and Sh=30 cm are employed in order to adjust the metered addition of the input gas II beforehand to that fixed catalyst bed in which the temperature is measured. The change in the molar ratio of hydrocarbon to be dehydrogenated to dehydrogenated hydrocarbon between entrance of the reaction gas into the gas inlet tube stub (4) and exit of the reaction gas from the gas outlet tube stub (5) provides the dehydrogenation conversion based on single pass through the reactor. The input gases II are injected such that the desired dehydrogenation conversion is attained.

The detailed configuration of the introduction of a guide finger (34) is shown by FIGS. 13 and 14 in longitudinal section.

These make clear that the guide finger (34) within the fixed catalyst bed is conducted within a (likewise closed) protective finger (35) which has an internal diameter in the range from 4 to 7 mm and an external diameter in the range from 6 to 9 mm. The gap between guide finger outer wall and protective finger inner wall is as low as possible. If appropriate, a remaining gap is filled with high-temperature thermal conductivity paste. This protective finger is welded on gas-tight resting on the inner wall (36) of the outer shell of the circular ring cylinder unit, so that no reaction gas can pass into the gap (38) between shell (1) and outer shell of the circular ring cylinder unit at this point. Outside the shell (1), the guide finger is conducted on the axis of symmetry of a flush tube (37) whose internal diameter is approx. 45 mm and whose external diameter is 50.8 mm. The length of a guide finger is 2000 mm and the length of the flush tube is 400 mm. The flush tube is sealed gas-tight with the aid of a flange (39), into which the guide finger is inserted gas-tight through a clamp ring seal (40).

On the outside of the shell (1), the flush tube is welded on gas-tight. The passage of the guide finger (34) through the shell (1) is not gas-tight. An inert gas (preferably molecular nitrogen, for example industrial nitrogen with up to 1% by volume of $O_2$, steam or mixtures thereof) is fed through a port (41) welded on at the flush tube, and, at the passage of the guide finger (34) through the shell (1), has access to the gap between shell (1) and outer shell of the circular ring cylinder unit (the inert gas is fed to some of the flush tubes indirectly via the gap (38)). FIG. 13 also shows the weld lip seal 17.

These inert gas streams will, in their entirety, generally be less than 1% by volume, usually even less than 0.1 or less than 0.01% by volume, based on the flow rate of the reaction gas (in $m^3$ (STP)).

FIGS. 15 and 16 show two bipods stabilized by a transverse strut in longitudinal section. They consist of tubes having an external diameter of 6 m and a wall thickness of 1 mm. The tubes forming the two legs are embedded into mounting cuboids (43) (30 mm×10 mm×20 mm (width×height×depth)).

Where the legs meet and, if appropriate, in the middle of the transverse strut, short sleeves (42) are embedded at right angles to the plane of intersection.

Several of these bipods are placed onto the grid sector before the fixed catalyst bed is poured in. The protective fingers (35) are then conducted through aforementioned sleeves (42) in order to stabilize the horizontal guiding of the guide fingers for the thermoelements and thus to counteract their sagging.

The coincident guide fingers (Sh=0 cm, Sh=30 cm) can be supported by a common bipod according to FIG. 16.

The adiabaticity of the axial tray reactor described can advantageously be improved further by mounting appropriate insulating materials (for example foam glass or mineral wool) on the exterior of the pressure vessel wall for thermal insulation (for example in a layer thickness of from 300 to 500 mm). The mounting can be effected, for example, by mounts which are secured to the outer wall (for example welded on).

The heterogeneously catalyzed partial dehydrogenation of propane to propylene addressed before the description of the design of the shaft reactor designed as an axial tray reactor can be carried out in this axial tray reactor, for example, as follows.

116 306 $m^3$ (STP)/h of a reaction gas which has the following contents are fed to the tray reactor through the gas inlet tube stub (the inert gas streams of $N_2$ into the reactor hood and into the flushing tubes (27) are neglected, since their amount, in total, is <0.01% by volume, based on the amount of reaction gas (in $m^3$ (STP)):

| | |
|---|---|
| propane | 34.44% by volume, |
| propylene | 0.2% by volume, |
| $N_2$ | 52.8% by volume, |
| $O_2$ | 3.04% by volume, |
| $CO_2$ | 1.61% by volume, |
| CO | 0.39% by volume, |
| $H_2$ | 0.09% by volume, |
| ethane | 0.12% by volume, |
| $H_2O$ | 7.22% by volume, |
| isobutene | 0.01% by volume, |
| acrylic acid | 0.04% by volume, |
| acrolein | 0.02% by volume, and |
| acetic acid | 0.02% by volume. |

The reaction gas has a temperature of 394° C. and an entrance pressure of 3.10 bar.

The input gas II 1 metered in between the first and the second fixed catalyst bed in flow direction of the reaction gas through the exit orifices A of the appropriate distribution boxes is 2930 $m^3$ (STP)/h of a mixture of air and steam which has the following contents:

| | |
|---|---|
| water | 34.9% by volume, |
| $N_2$ | 51.4% by volume, and |
| $O_2$ | 13.7% by volume. |

The temperature of the input gas II 1 is 450° C. and its pressure is 2.9 bar.

The input gas II 2 metered in between the second and the third fixed catalyst bed in flow direction of the reaction gas through the exit orifices A of the appropriate distribution boxes is 2600 $m^3$ (STP)/h of a mixture of air and steam which has the following contents:

| | |
|---|---|
| water | 54.33% by volume, |
| $N_2$ | 36.09% by volume, and |
| $O_2$ | 9.58% by volume. |

The temperature of the input gas II 2 is 450° C. and its pressure is 2.8 bar. A product gas mixture leaves the tray reactor in an amount of 120 754 $m^3$ (STP)/h through the gas outlet tube stub (5) and has the following contents:

| | |
|---|---|
| propane | 24.95% by volume, |
| propylene | 5.77% by volume, |
| $N_2$ | 49.865% by volume, |
| $O_2$ | 0% by volume, |
| $CO_2$ | 3.03% by volume, |
| CO | 0.35% by volume, |
| $H_2$ | 4.13% by volume, |
| methane | 0.01% by volume, |
| ethane | 0.11% by volume, |
| ethylene | 0.01% by volume, |
| $H_2O$ | 11.98% by volume, and |
| acrylic acid | 0.01% by volume. |

The temperature of the product gas mixture is 501° C. and the pressure of the product gas mixture is 2.71 bar.

As the input gas stream I 1, a gas mixture flows out of the first fixed catalyst bed in flow direction of the reaction gas in an amount of 120 754 $m^3$ (STP)/h (this corresponds to a flow rate W1 of 1.1 m/s) and has the following contents:

| | |
|---|---|
| propane | 30.16% by volume, |
| propylene | 3.03% by volume, |
| $N_2$ | 51.03% by volume, |
| $O_2$ | 0% by volume, |
| $CO_2$ | 2.36% by volume, |
| CO | 0.372% by volume, |
| $H_2$ | 2.14% by volume, |
| methane | 0.001% by volume, |
| ethane | 0.116% by volume, |
| ethylene | 0.004% by volume, |
| $H_2O$ | 9.75% by volume, and |
| acrylic acid | 0.022% by volume. |

The temperature of the input stream I 1 is 496°0 C. and its pressure is 2.9 bar.

As the input gas stream I 2, a gas mixture flows out of the second fixed catalyst bed in flow direction of the reaction gas in an amount of 127 180 $m^3$ (STP)/h (this corresponds to a flow rate of 1.33 m/s) and has the following contents:

| | |
|---|---|
| propane | 26.85% by volume, |
| propylene | 4.65% by volume, |
| $N_2$ | 50.29% by volume, |
| $O_2$ | 0% by volume, |
| $CO_2$ | 2.75% by volume, |
| CO | 0.359% by volume, |
| $H_2$ | 3.34% by volume, |
| methane | 0.002% by volume, |
| ethane | 0.113% by volume, |
| ethylene | 0.005% by volume, |
| $H_2O$ | 11.13% by volume, and |
| acrylic acid | 0.013% by volume. |

The temperature of the input gas stream I 2 is 499° C. and its pressure is 2.8 bar.

The directions of all individual input gas II 1 streams exiting from the exit orifices A 1 (these are the exit orifices A in the distribution boxes for the input gas II 1 of the first circular ring cylinder unit in flow direction of the reaction gas) in the theoretical absence of the input gas stream I 1 enclose an angle $\alpha$ of 90° with the flow direction of the input gas stream I 1.

The directions of all individual input gas II 2 streams exiting from the exit orifices A 2 (these are the exit orifices A in the distribution boxes for the input gas II 2 of the second circular ring cylinder unit in flow direction of the first reaction gas) in the theoretical absence of the input gas stream I 2 enclose an angle α of 90° with the flow direction of the input gas stream I 2.

The induction time J 1 of the reaction gas input mixture 1 (is conducted into the second circular ring cylinder unit in flow direction of the reaction gas) is 0.735 second.

When the temperature of the reaction gas input mixture 1 is increased to 550° C., the induction time falls to 0.15 second.

a corresponding manner to a temperature increase, a pressure increase also shortens the induction time J.

induction time J 2 of the reaction gas input mixture 2 (is conducted into the third circular ring cylinder unit in flow direction of the reaction gas) is 0.761 second.

When the temperature of the reaction gas input mixture 2 is increased to 550° C., the induction time falls to 0.15 second.

The distance D1 of all exit orifices A1 from the relevant fixed catalyst bed is 5 mm.

The distance D2 of all exit orifices A2 from the relevant fixed catalyst bed is 5 mm.

In alternative embodiments, D1 and D2 may also each be adjusted uniformly to any other value in the range from 5 mm to 10 mm.

In a projection of all exit orifices A1 in flow direction of the input gas stream I 1 into the projection plane E1 at right angles to the flow direction of the input gas stream I 1, the number ZA1 of exit orifice centers present in any $m^2$ in the projection surface area covered by the input stream I 1 is ≥50.

The distance from one exit orifice center to the closest exit orifice center in the projection plane is not more than 100 mm.

In a projection of all exit orifices A2 in flow direction of the input stream I 2 into the projection plane E2 at right angles to the flow direction of the input stream I 2, the number ZA2 of exit orifice centers present in any $m^2$ in the projection surface area covered by the input stream I 2 is ≥50.

The distance from one exit orifice center to the closest exit orifice center in the projection plane is not more than 100 mm.

As the reaction gas mixture input stream 1 passes through the fixed catalyst bed present in the second circular ring cylinder unit in flow direction of the reaction gas, 6.19 mol % of the propane present in the reaction gas mixture input stream 1 is converted to propylene.

As the reaction gas mixture input stream 2 passes through the fixed catalyst bed present in the third circular cylinder unit in flow direction of the reaction gas, 3.09 mol % of the propane present in the reaction gas mixture input stream 2 is converted to propylene.

The product gas mixture which leaves the tray reactor through the gas outlet tube stub (5) can then be used in a manner known per se in order to oxidize the propylene present therein, accompanied by the propane present therein, partially in a downstream heterogeneously catalyzed partial oxidation to acrolein and/or acrylic acid as the target product.

The procedure may, for example, be as in the documents DE-A 10 2005 061 626, DE-A 10 2005 057 197, DE-A 10 2005 052 923, DE-A 10 2005 052 917, DE-A 10 2005 022 798, DE-A 10 2005 009 885, DE-A 10 2005 010 111, DE-A 10 2004 032 129, DE-A 10 2005 013 039, WO 03/076370, DE-A 102 11 275, WO 01/96270, DE-A 10 2005 056 377 and the prior art cited in these documents. In particular, the procedure may be as described in DE-A 10 2004 032 129 and in DE-A 10 2005 013 039 or in DE-A 10 2005 022 798.

Target product is normally subsequently removed from the product gas mixture of the partial oxidation and, from the remaining residual gas, at least a portion comprising propane and, if appropriate, unconverted propylene for generation of the reaction gas fed through the gas inlet tube stub of the axial tray reactor is recycled into the heterogeneously catalyzed partial dehydrogenation.

In the manner corresponding to the above, the 116 309 $m^3$ (STP)/h of reaction gas fed through the gas inlet tube stub of the axial tray reactor described was obtained by combining (for example as in FIG. 10 of WO 2004/067164) 8063 $m^3$ (STP)/h of crude propane of the specification

| | | |
|---|---|---|
| propane | ≥98.0% | by volume, |
| propylene | ≤0.11% | by volume, |
| n-butane | <0.001% | by volume, |
| isobutane | <0.05% | by volume, |
| ethane | <1.5% | by volume, |
| ethylene | <0.02% | by volume, and |
| other $C_4$ hydrocarbons | <0.001% | by volume, |

of temperature 20° C. and pressure 4 bar, and 102 961 $m^3$ (STP)/h of residual gas of such a partial oxidation which, at a temperature of 104° C. and a pressure of 3.3 bar, has the following contents:

| | | |
|---|---|---|
| propane | 31.18% | by volume, |
| propylene | 0.215% | by volume, |
| $N_2$ | 59.69% | by volume, |
| $O_2$ | 3.44% | by volume, |
| $CO_2$ | 1.81% | by volume, |
| CO | 0.444% | by volume, |
| $H_2$ | 0.098% | by volume, |
| ethane | 0.06% | by volume, |
| ethylene | 0.003% | by volume, |
| $H_2O$ | 2.96% | by volume, |
| acrylic acid | 0.04% | by volume, |
| acrolein | 0.03% | by volume, and |
| acetic acid | 0.03% | by volume. |

To combine the two gas streams, they are mixed intensively with one another, for example, in a static mixer installed into a pipeline.

It is advantageous when the aforementioned combination and the time of feeding into the gas inlet tube stub are as close as possible in time.

The combination first forms a gas mixture with P=3.21 bar and T=95.7° C. Indirect heat exchange with the product gas mixture leaving the gas outlet tube stub (S) brings it to the temperature of 394° C. and the entrance pressure of 3.10 bar.

The target product can be removed from the product gas mixture obtained in the heterogeneously catalyzed gas phase partial oxidation of propylene to acrolein and/or acrylic acid in at least one removal step in a manner known per se. The procedure is normally to convert the at least one target product in a basic removal step from the gas phase to the liquid phase (the product gas mixture is, if appropriate, cooled beforehand). This can be done, for example, by partial or full and, if appropriate, fractional condensation of the target product (for example acrolein and/or acrylic acid) and/or by absorption of the at least one target product from the product gas mixture into an aqueous or organic solvent (i.e. fractional condensation and/or absorption with water or aqueous solution can also be employed superimposed on one another). Preference is generally given to fractional condensation and/or absorption in water or in aqueous solutions as the basic removal step. In the case of acrylic acid and/or acrolein as the target product, suitable absorbents are, for example, water, aqueous solutions of lower carboxylic acids and hydrophobic organic solvents, such as mixtures of diphenyl and diphenyl ether (e.g. Diphyl®) or mixtures of Diphyl (from 75 to 99.9% by weight) and dimethyl phthalate (from 0.1 to 25% by weight). In the case of acrylic acid, the product gas mixture comprising the target product will preferably be fractionally condensed. For example, the basic removal (especially in the case of acrylic acid) can be effected as described in the following documents (cf., for example, EP-A 1 388 533, EP-A 1 388 532, DE-A 102 35 847, EP-A 792 867, WO 98/01415, EP-A 10 15 411, EP-A 10 15 410, WO 99/50219, WO 00/53560, WO 02/09839, DE-A 102 35 847, WO 03/041833, DE-A 102 23 058, DE-A 102 43 625, DE-A 103 36 386, EP-A 854 129, U.S. Pat. No. 4,317,926, DE-A 198 37 520, DE-A 196 06 877, DE-A 190 50 1325, DE-A 102 47 240, DE-A 197 40 253, EP-A 695 736, EP-A 982 287, EP-A 10 41 062, EP-A 11 71 46, DE-A 43 08 087, DE-A 43 35 172, DE-A 44 36 243, DE-A 199 24 532, DE-A 103 32 758 and DE-A 199 24 533). An acrylic acid removal can also be undertaken as described in EP-A 982 287, EP-A 982 289, DE-A 103 36 386, DE-A 101 15 277, DE-A 196 06 877, DE-A 197 40 252, DE-A 196 27 847, EP-A 920 408, EP-A 10 68 174, EP-A 10 66 239, EP-A 10 66 240, WO 00/53560, WO 00/53561, DE-A 100 53 086 and EP-A 982 288. Preference is given to removing as described in FIG. 7 of WO/0196271 or as described in DE-A 10 2004 032 129 and its equivalent patents. Favorable modes of removal are also the processes described in the documents WO 2004/063138, WO 2004/035514, DE-A 102 43 625 and DE-A 102 35 847. The further processing of crude acrylic acid obtained can be effected, for example, as described in the documents WO 01/77056, WO 03/041832, WO 02/055469, WO 03/078378 and WO 03/041833.

A common feature of the above separating processes is that a residual gas stream which comprises essentially those constituents of the product gas mixture whose boiling point at standard pressure (1 bar) is ≤−30° C. (i.e. the constituents which are difficult to condense or else volatile) normally remains, for example, at the top of the particular separating column comprising, for example, separating internals and in whose lower section the product gas mixture comprising the at least one target product is fed, normally after preceding direct and/or indirect cooling.

In the lower section of the separating column, the less volatile constituents of the product gas mixture, including the particular at least one target product and secondary components of similar volatility to the target product, are normally obtained in the condensed phase.

The residual gas constituents are normally primarily propane, if appropriate propylene unconverted in the partial oxidation, molecular oxygen and frequently the other inert diluent gases which are also used in the partial oxidation, for example nitrogen and carbon dioxide. Depending on the separation process employed, steam may be present in the residual gas only in traces or in amounts of up to 20% by volume. This residual gas can be (and generally is) used to proceed as described.

At this point, it should be emphasized once again that acrylic acid is basically removed from a partial oxidation product gas mixture which comprises acrylic acid as the target product and has been obtained as described preferably in such a way that the product gas mixture which has been cooled by direct and/or indirect cooling beforehand if appropriate is fractionally condensed, ascending (for example into itself) in a column comprising separating internals with side draw removal of crude acrylic acid, and/or absorbed with water or aqueous solution, as described by way of example in WO 2004/035514 and DE-A 102 43 625. The crude acrylic acid withdrawn is subsequently preferably subjected to a suspension crystallization, and the acrylic acid suspension crystals formed are preferably removed from remaining mother liquor by means of a wash column. Advantageously, the wash liquid used is the melt of acrylic acid crystals removed beforehand in the wash column. Furthermore, the wash column is preferably one with forced transport of the crystal bed. It is more preferably a hydraulic wash column (for example a TNO wash column) or a mechanical wash column. For specific details, the description of WO 01/77056, of WO 03/041832 and of WO 03/041833 may be followed. In other words, remaining mother liquor is preferably recycled into the fractional condensation (cf. also EP-A 10 15 410). The secondary component outlet is normally below the side draw of the crude acrylic acid as a purge stream.

Using only one crystallization stage, it is thus possible to obtain acrylic acid having a purity of ≥99.8% by weight which is outstandingly suitable for producing superabsorbents based on poly-Na acrylate.

Otherwise, the profile of requirements laid down in DE-A 102 45 585 and in DE-A 102 46 119 also applies to the process according to the invention.

Processes according to the invention are generally also those in which the process according to the invention for heterogeneously catalyzed partial dehydrogenation is followed by at least one heterogeneously catalyzed partial oxidation of the at least one dehydrogenated hydrocarbon.

Figure 19:
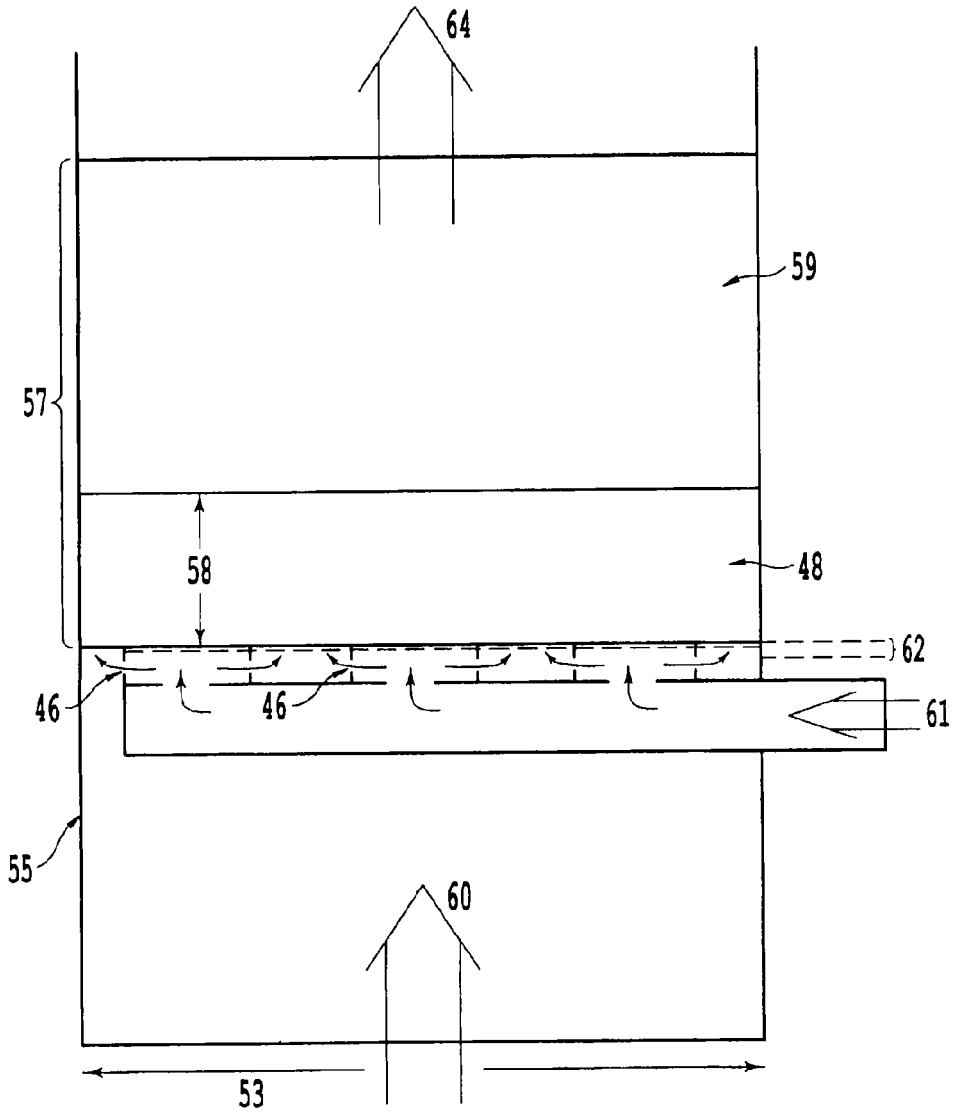
FIG. 19: shows the top view on a longitudinal section of a cuboidal shaft reactor portion.
Figure 20:
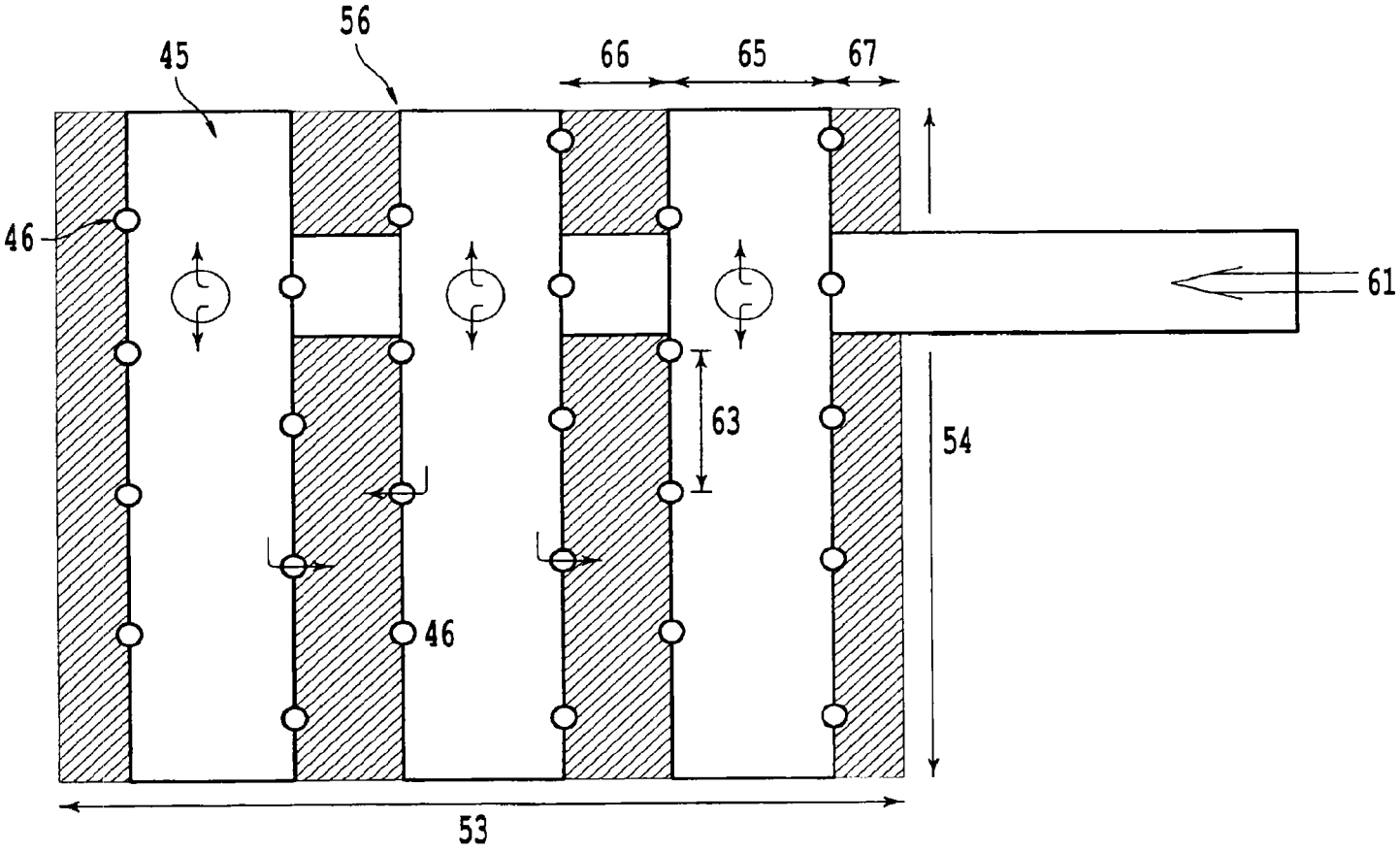
FIG. 20: shows the top view on a cross section of the same cuboidal shaft reactor to which FIG. 19 refers.

The numerals in FIGS. 19 and 20 have the following meaning:

53=length (840 mm) of edge "a" of the base surface of the reactor shaft;

54=length (900 mm) of edge "b" of the base surface of the reactor shaft;

55=edge "c" of the reactor shaft;

56=projection plane E;

57=fixed catalyst bed;

48=bed of inert shaped bodies;

58=length X (220 mm) of bed 6;

59=catalytically active bed;

60=input gas stream I having a volume flow rate V1 and a flow rate W;

61=input gas II comprising molecular oxygen and having a volume flow rate V2;

46=exit orifice A (total number of orifices A in plane E=26, accordingly ZA=26/(a×b)=34/m2);

62=distance D (about 20 mm);

63=distance d (150 mm) from one exit orifice center to the closest exit orifice center;

$d=150\ mm<2\sqrt{1m^2/ZA}=343\ mm$;

X/d=220 mm/150 mm=1, 47;

64=product gas;

45=one of three cuboidal metering boxes belonging to the line system for metering in input gas II;

65=length (150 mm) of the edge of a metering box which is parallel to edge a;

66=separation (130 mm) between two metering boxes; and

67=separation (65 mm) between edge b and the edge of the metering box parallel to it.

EXAMPLE

A cuboidal (shaft) reactor reproduction (44) was used. The interior of the cuboid with a wall thickness of 3 mm (all elements of the reactor reproduction were manufactured from 1.4541 stainless steel) had the following dimensions. The base surface was 840 mm (edge a)×900 mm (edge b). The height (edge c) of the cuboidal reactor reproduction was 1200 mm.

60 cm above the base surface of the reactor reproduction (the measure is based on the distance from the base surface up to the upper edge a* of the metering boxes (distribution boxes)) were mounted, in the interior of the reactor reproduction, with their longest edge b* parallel to the edge b, three identical, likewise cuboidal metering boxes (45) with the rectangular cross section a*×c*. The wall thickness of these metering boxes was 2 mm. The edges a* were parallel to the edge a and had a length of 15 cm. The edges c* were parallel to the edge c and had a length of 4 cm. The separation between two metering boxes was 13 cm. The middle of the three distribution boxes was arranged centrally with its edge a* at the cuboid width a=840 mm. The edge b* had a length of 900 mm. The distribution boxes were each welded onto the delimiting surfaces a×c by their delimiting surfaces a*×c*. At the top, the cuboidal reactor reproduction was open (i.e. it had no lid), and closed at the bottom and at the four sides.

In the two rectangular surfaces c*×b* of a metering box were disposed circular exit orifices A (46) with the diameter 3 mm arranged like a string of successive beads, the string having a separation of 5 mm from the edge b* which faces toward the base surface a×b and forming a parallel to this edge.

The distance from one exit orifice A to the next exit orifice A on the "string of beads" was (measured from center to center) 10 cm. The exit orifices A of mutually opposite rectangular surfaces c*×b* of adjacent rectangular boxes were opposite one another with a gap.

A perforated plate (47) with a plate thickness of 3 mm was placed onto the metering boxes (45) (over the cross section a×b). The shape of the holes was uniformly oval. Their transverse dimension was 3 mm and their longitudinal dimension was 1.5 cm. The opening ratio of the perforated sheet was 30% (% opening ratio=(total of the permeable surface areas/total surface area)×100). The hole centers were distributed uniformly in square pitch.

An inert bed (48) of bed height 20 cm of 7 mm×7 mm×4 mm (external diameter×height×internal diameter) steatite rings was poured onto the perforated sheet. A uniform metal mesh was laid onto this inert bed and was composed of longitudinal and transverse metal wires.

The distance between two closest parallel metal wires was 2 mm. A grid (49) was placed onto this metal mesh and, just like the metal mesh, extended over the entire cross section a×b. The height of the grid (parallel to the edge c) was 10 cm. Otherwise, the grid had a honeycomb structure. The individual honeycomb had a square cross section with an inner surface of 3 cm×3 cm. The wall thicknesses of the grid were 1 mm.

Below the metering boxes was disposed a metering line (50) which ran parallel to the edge a (the distance to the nearest edge a was 10 cm) and was inserted through a corresponding orifice of the wall b×c and welded into it in a gas-tight manner. The metering line had a square cross section of 10 cm×10 cm. Its length extended up to the end of the edge a* of the third metering box.

Below the particular distribution box, the metering line had a circular orifice of diameter 8 cm which coincided with a corresponding (centrally mounted) circular orifice in the surface a*×b* facing toward the base surface a×b and was welded onto it. The length of the metering line was 800 m.

40 $m^3$/h of a mixture (simulated the input gas II) composed of 10% by volume of $CO_2$ and 90% by volume of air were fed into this metering line (T=25° C., P=1.1 bar).

At a distance of 10 cm, a perforated plate (51) was welded into the cuboidal reactor reproduction below the metering line and extended over the entire cross-sectional area a×b. The holes of the perforated plate (plate thickness 3 mm) had a diameter of 1 cm. The hole centers were distributed uniformly in a square pitch. The orifice ratio of the perforated plate was 6%.

Below the aforementioned perforated plate, a circular stub (52) (internal diameter 300 mm) led into the cuboidal reactor reproduction. Its distance from the base surface a×b was 5 cm. Its distance from the closest surface a×c was 10 cm.

The surface b×c through which the stub was inserted was opposite the surface b×c through which the metering line was inserted (when the metering line and the stub were theoretically extended in the same flow direction, the extension lines essentially coincided.

2500 $m^3$/h of air (T=25° C., P=1.1 bar) were conducted through the stub into the cuboidal reactor reproduction (simulated the input gas stream I).

With the aid of an Ultramat 22P from Siemens (aspirates gas mixture and conducts it through a cuvette, of whose contents the $CO_2$ content is determined by UV spectroscopy in comparison with the behavior of the contents of a comparative cuvette), the $CO_2$ content was determined in the individual quadratic honeycombs of the honeycomb grid.

The theoretical mean $CO_2$ concentration was 0.16% by volume.

The maximum measured $CO_2$ concentration was 0.30% by volume.

The minimum measured $CO_2$ concentration was 0.02% by volume.

Figure 1:
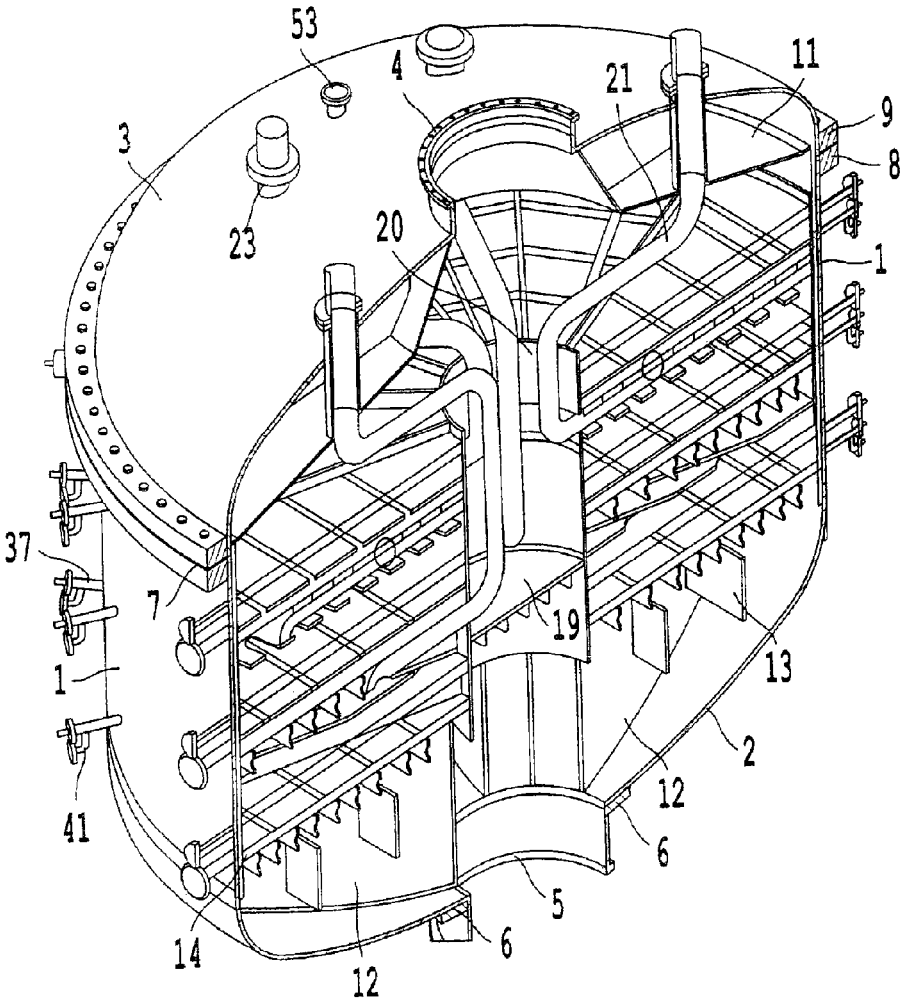
FIG. 1: top view on a longitudinal section of a shaft reactor configured as a tray reactor suitable in accordance with the invention
Figure 2:
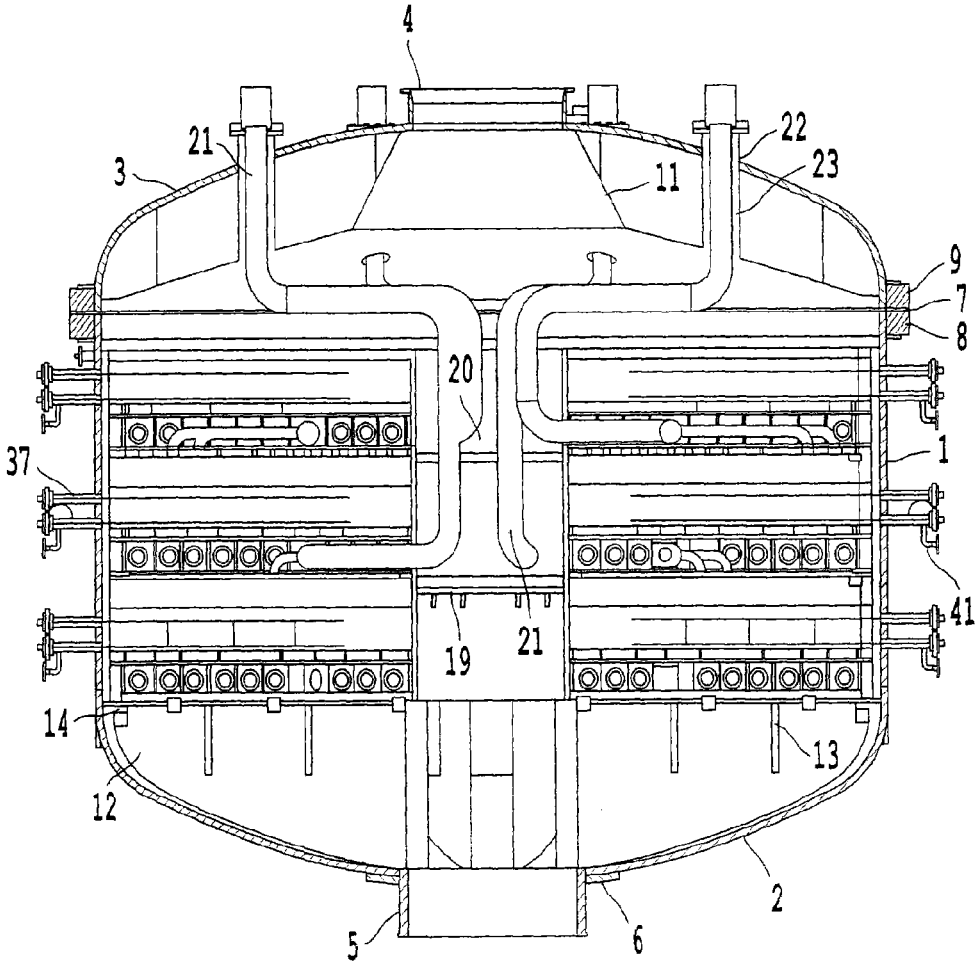
FIG. 2: front view of a longitudinal section of a shaft reactor configured as a tray reactor suitable in accordance with the invention
Figure 3:
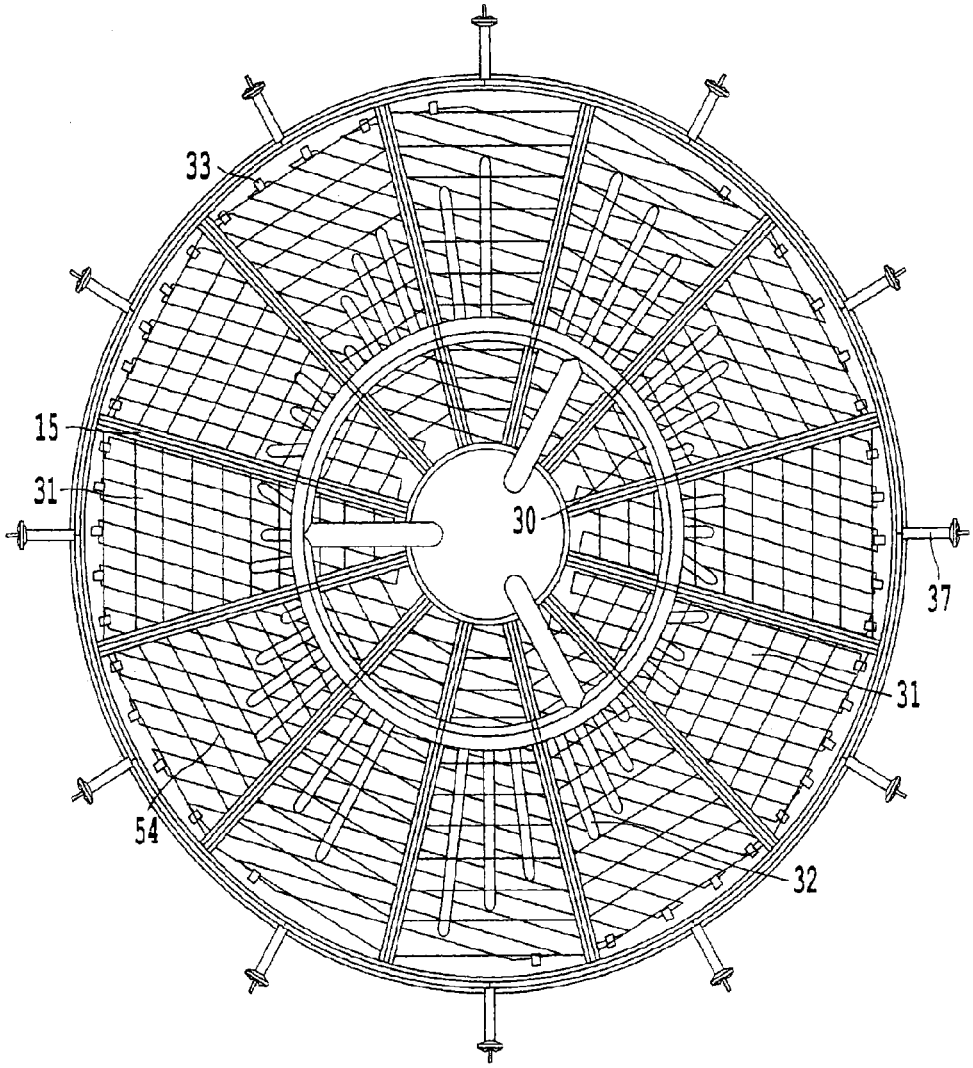
FIG. 3: top view on a circular ring cylinder unit with omission of the grid
Figure 4:
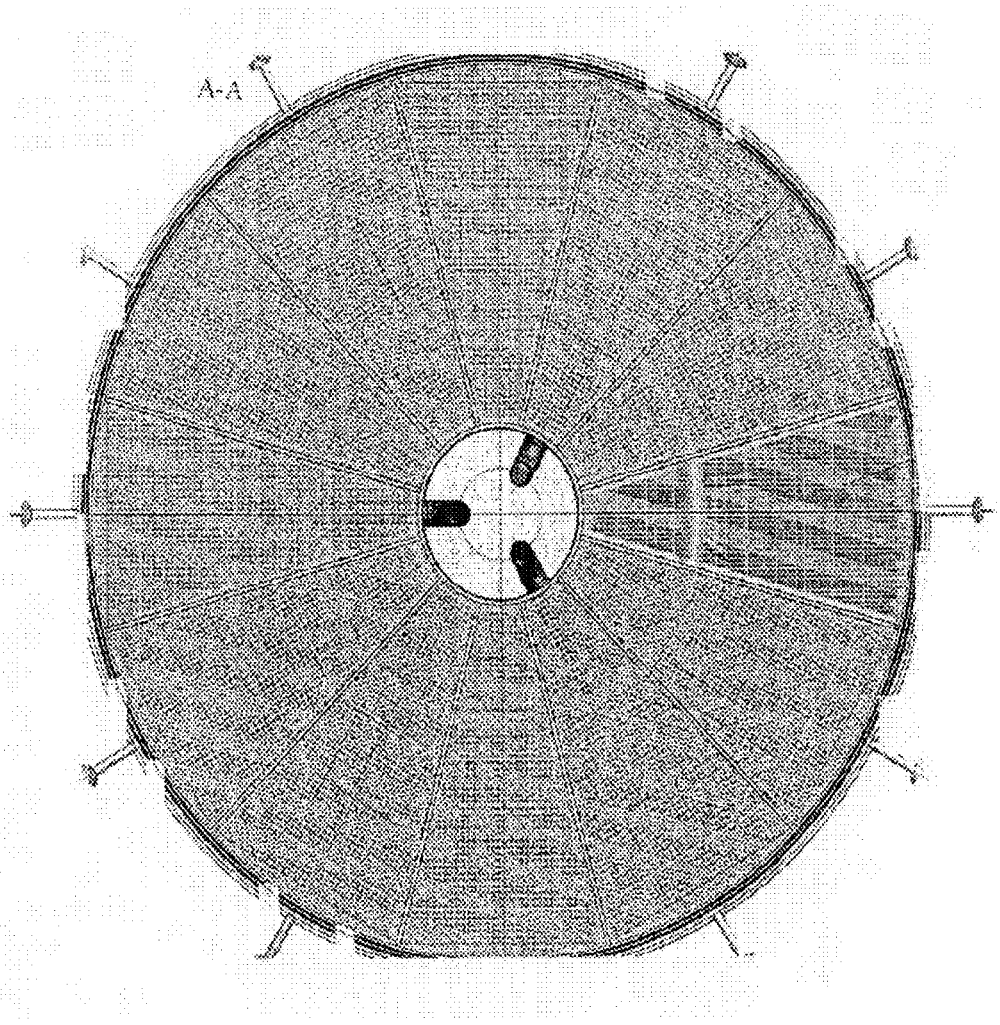
FIG. 4: plan view on a circular ring cylinder unit with grid and network of metal wire mounted thereon
Figure 5:
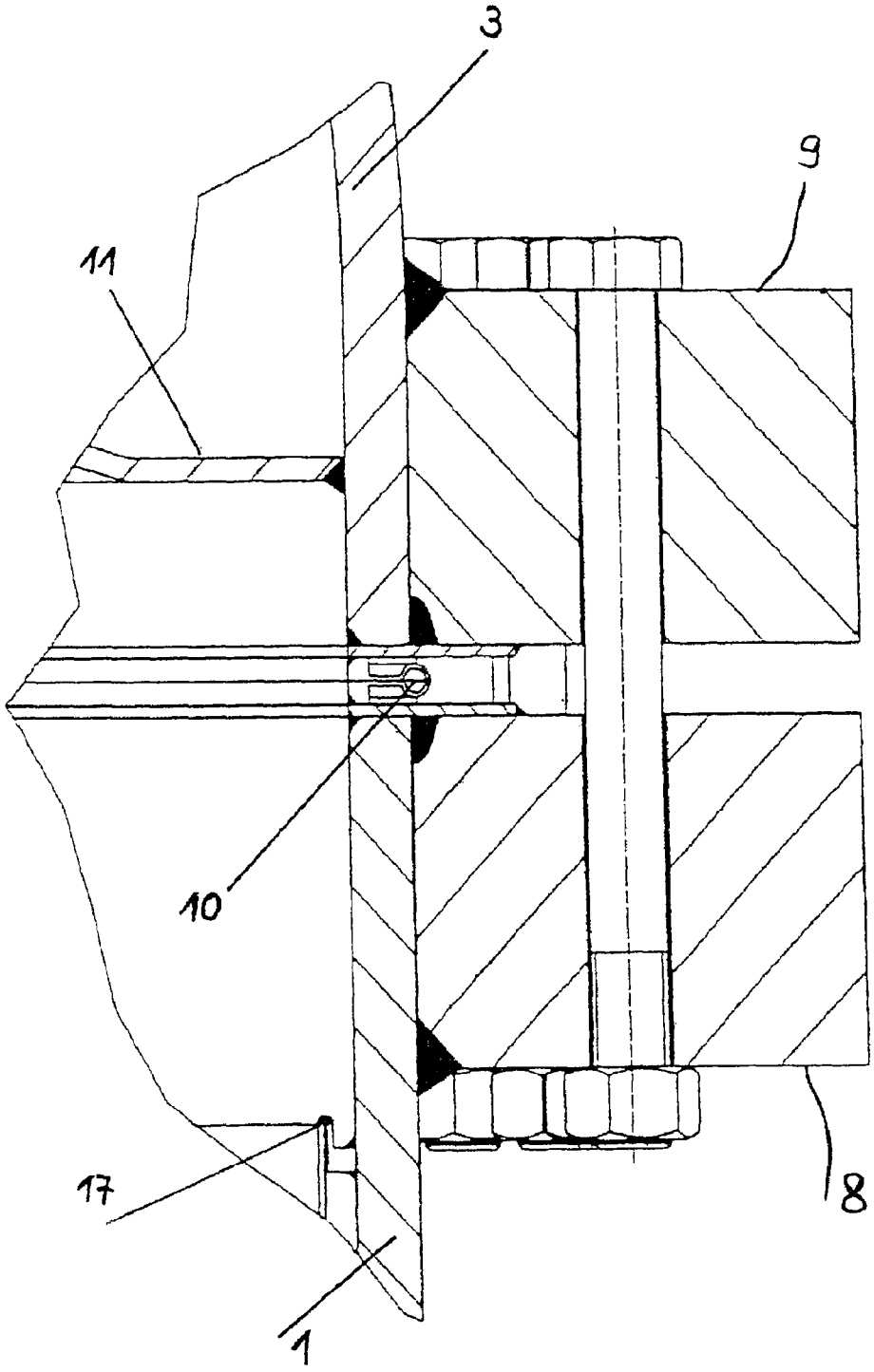
FIG. 5: flange bond between circular cylinder shell (1) and upper reactor hood
Figure 6:
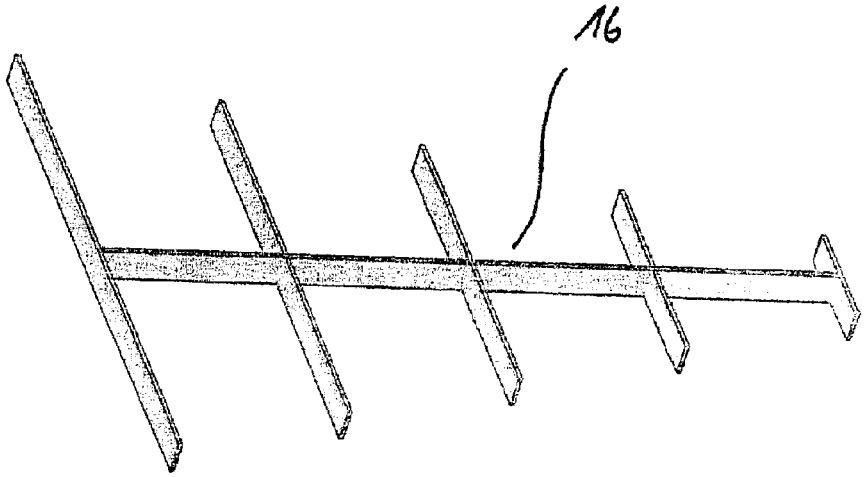
FIG. 6: pouring aid
Figure 7:
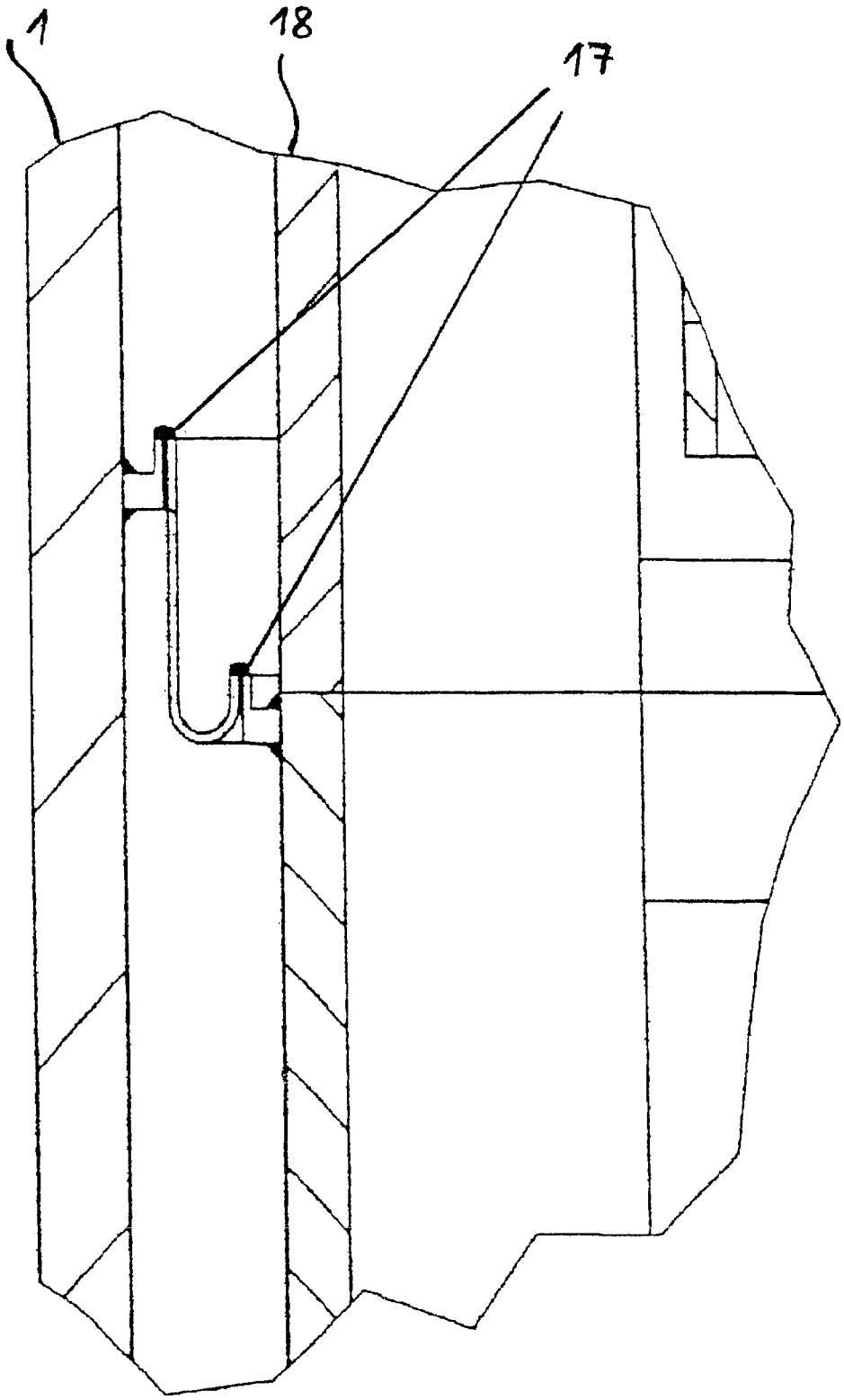
FIG. 7: weld lip seal between circular cylinder shell (1) and outer shell of a circular ring cylinder unit at the level of the top circular ring
Figure 8:
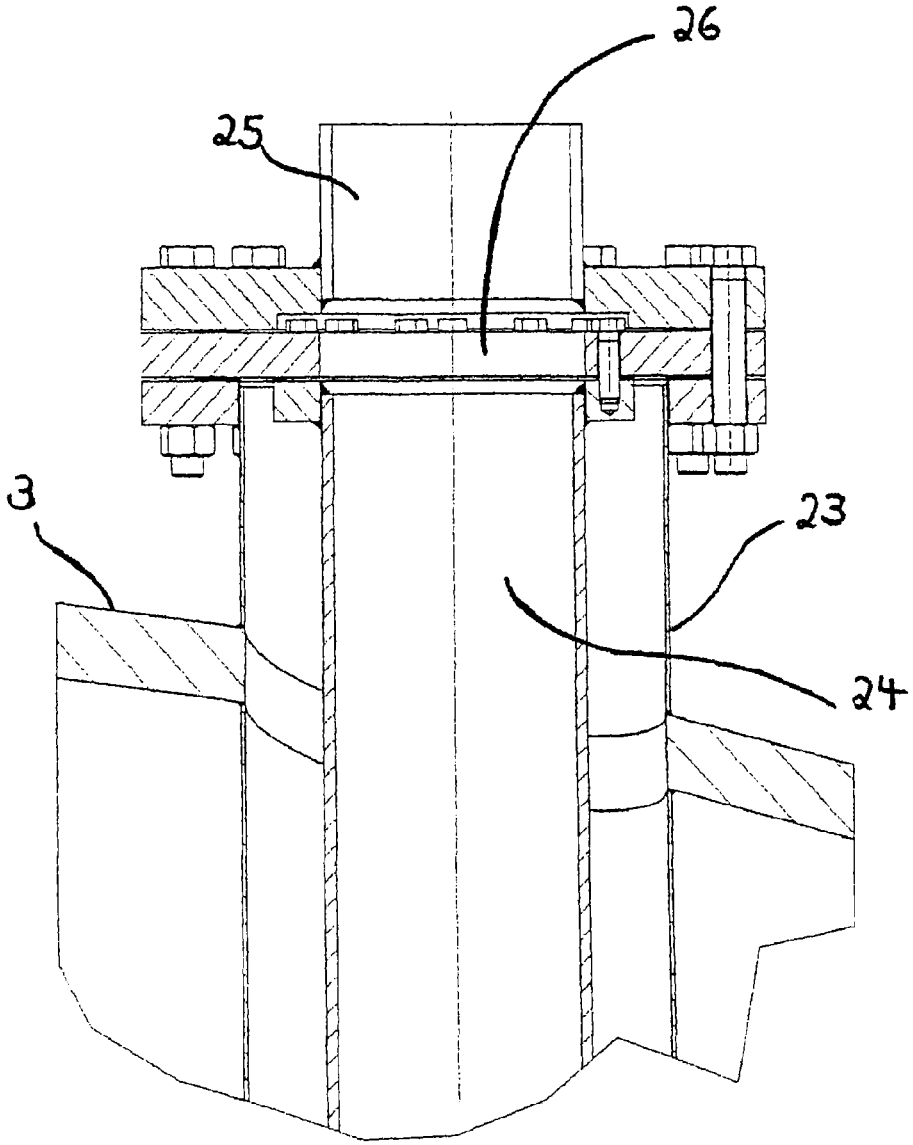
FIG. 8: three-piece transition of a tube conducting input gas II into the entrance stub of the upper reactor hood
Figure 9:
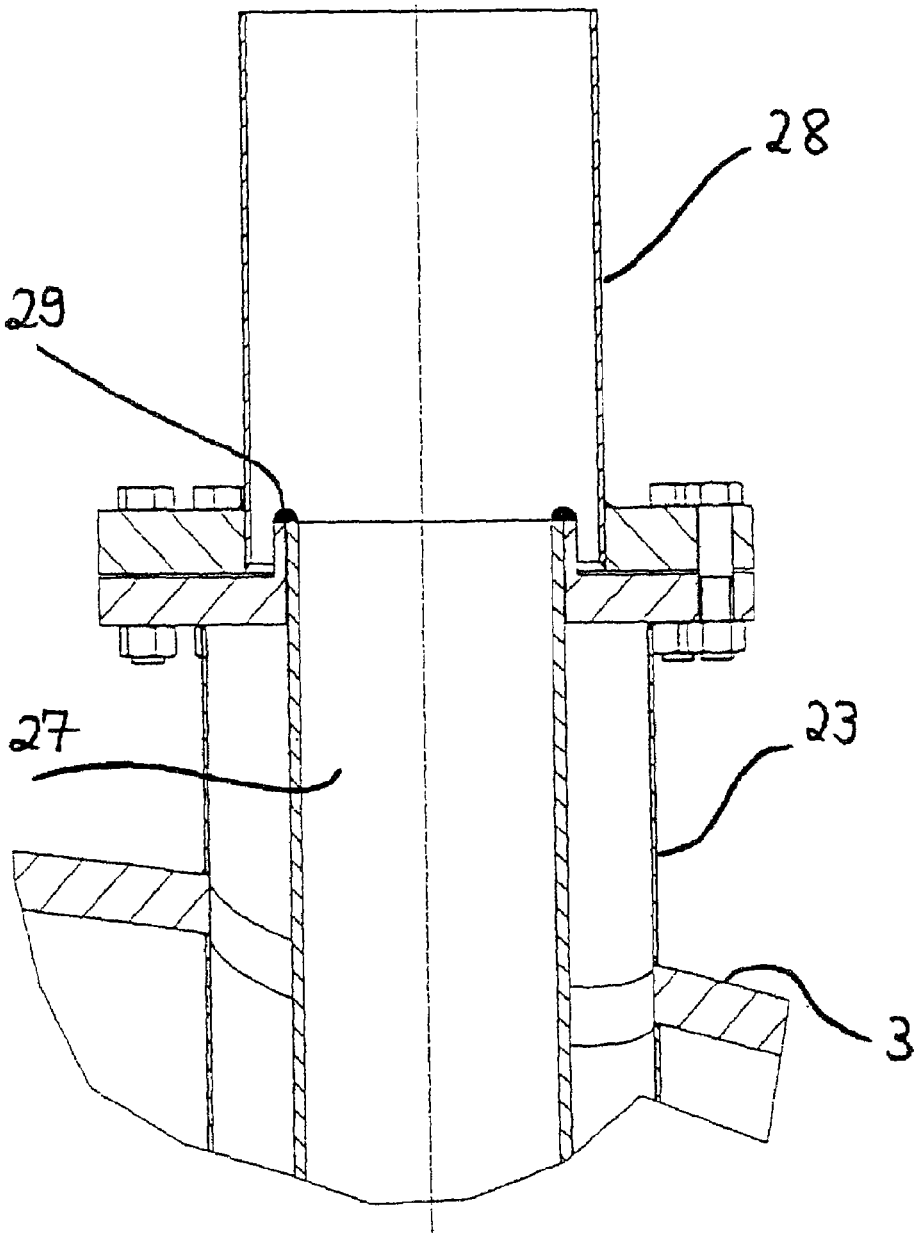
FIG. 9: two-piece transition of a tube conducting input gas II into the entrance stub of the upper reactor hood
Figure 10:
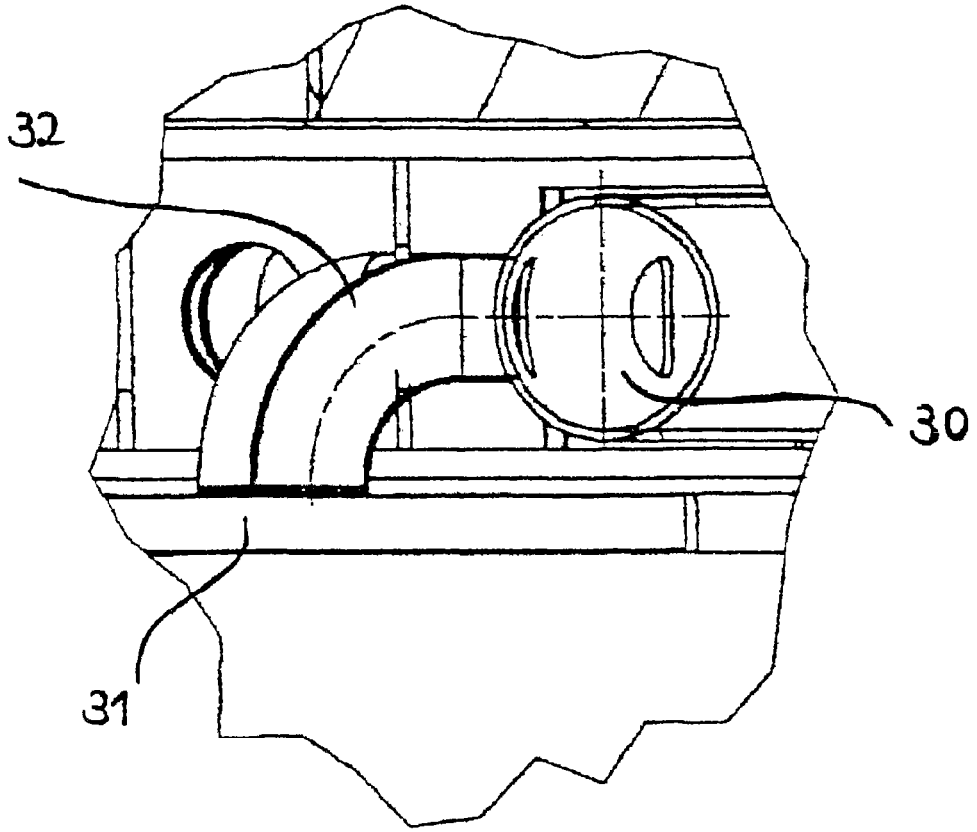
FIG. 10: opening of distribution tubes into metering boxes
Figure 11:
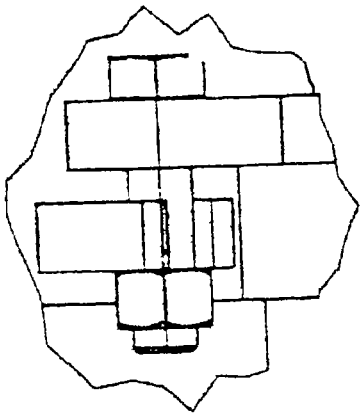
FIG. 11: side view of a mount configured in positively locking form for a distribution box
Figure 12:
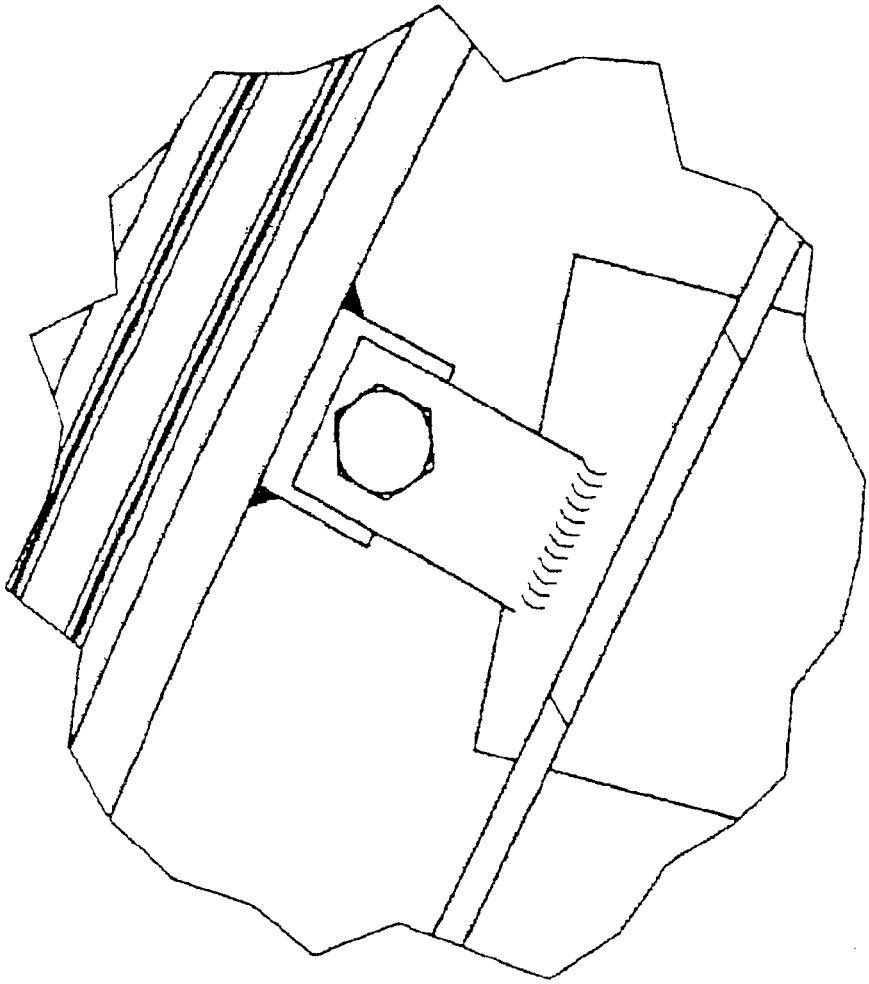
FIG. 12: plan view of the mount shown in side view in FIG. 11
Figure 13:
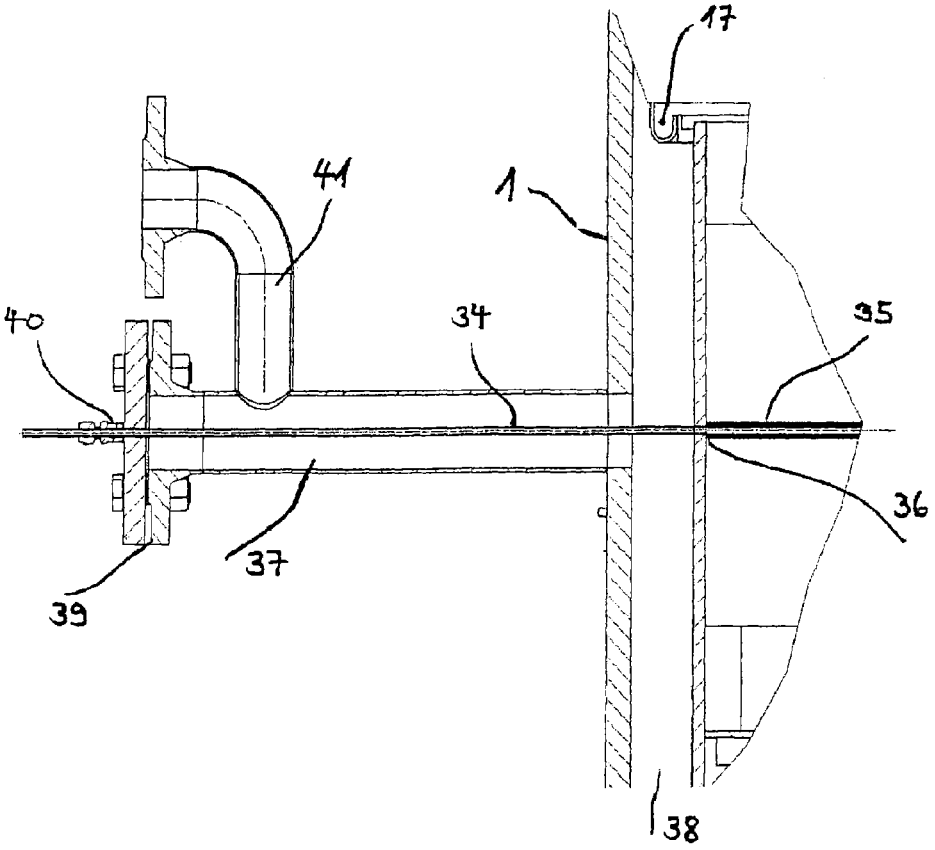
FIG. 13: introduction of a thermoelement into a fixed catalyst bed
Figure 14:
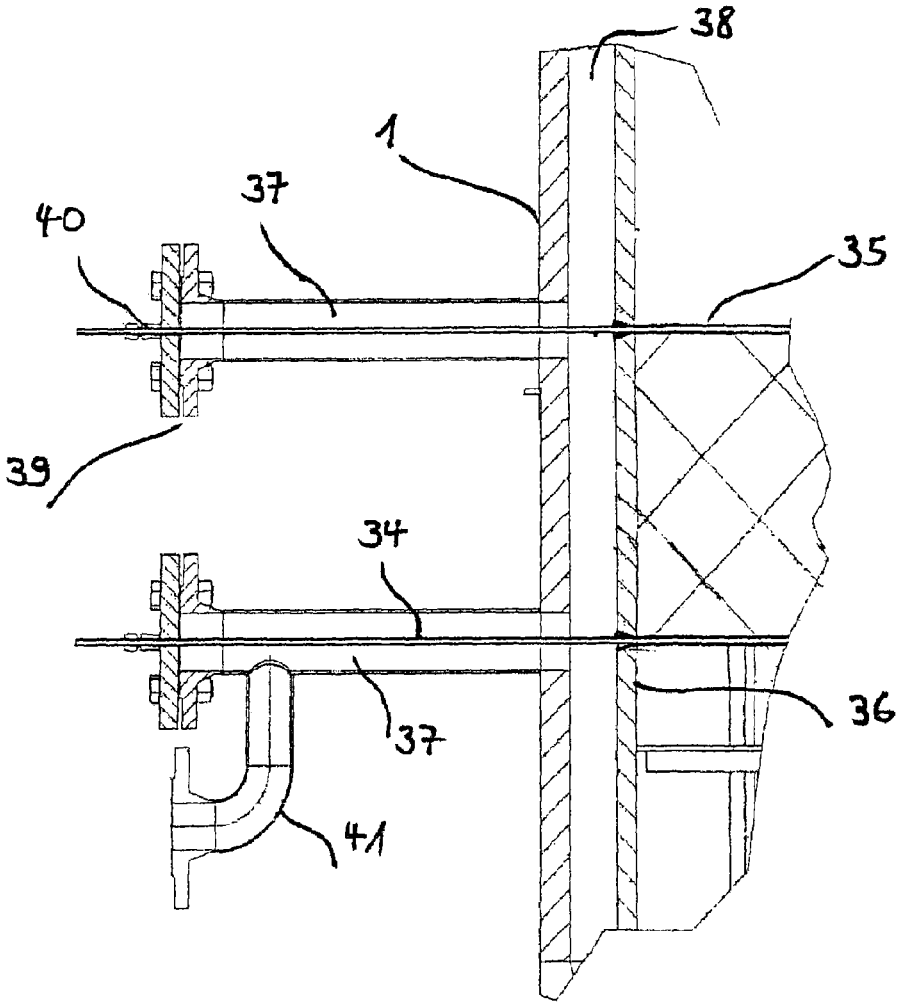
FIG. 14: introduction of two thermoelements which are conducted one on top of the other within the fixed catalyst bed and are coincident
Figure 15:
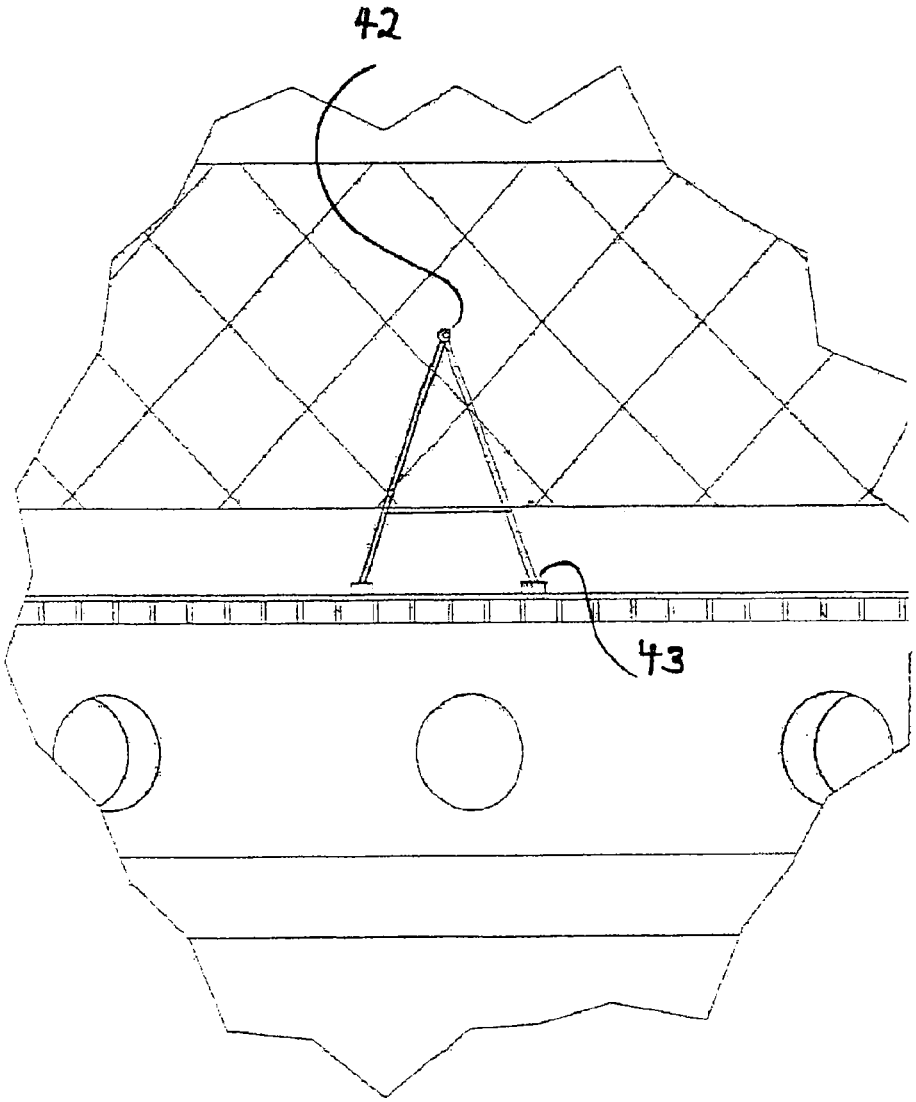
FIG. 15: bipod for supporting a thermoelement guide finger
Figure 16:
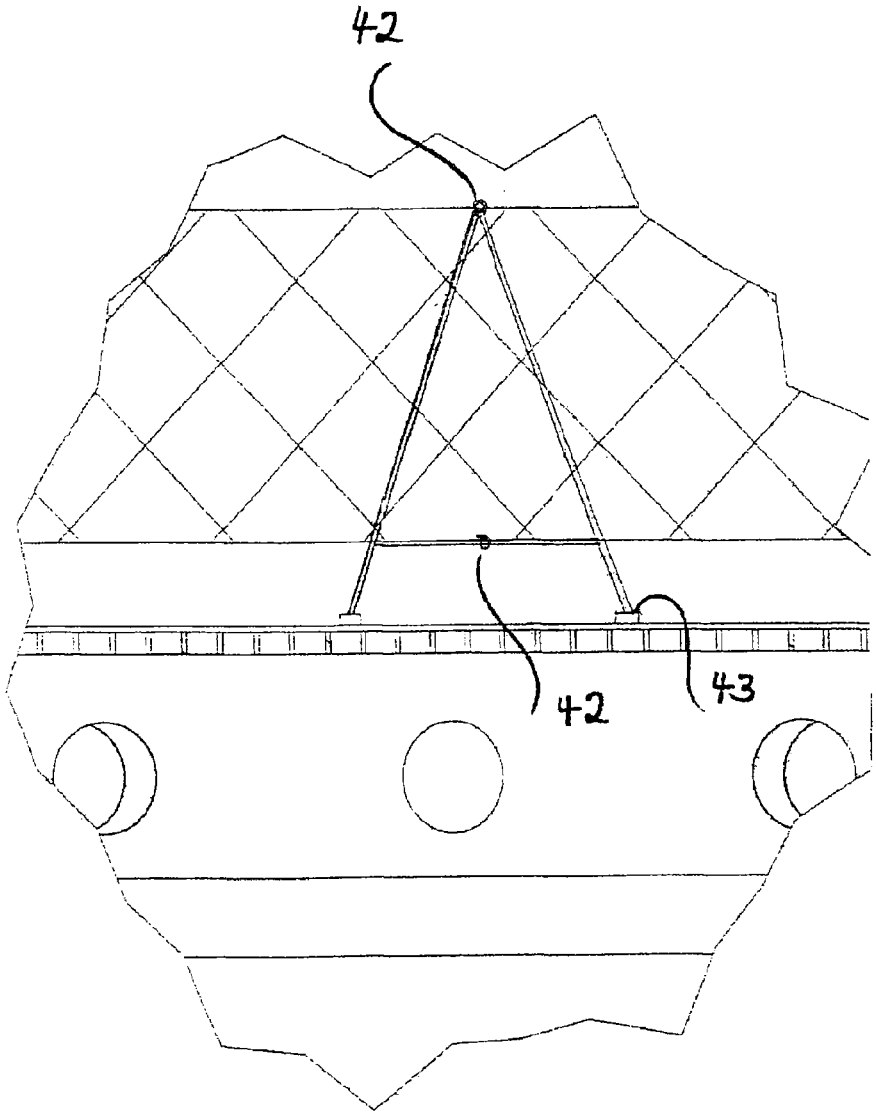
FIG. 16: bipod for supporting the guide fingers of two thermoelements which are conducted one on top of the other within the fixed catalyst bed and are coincident
Figure 17:
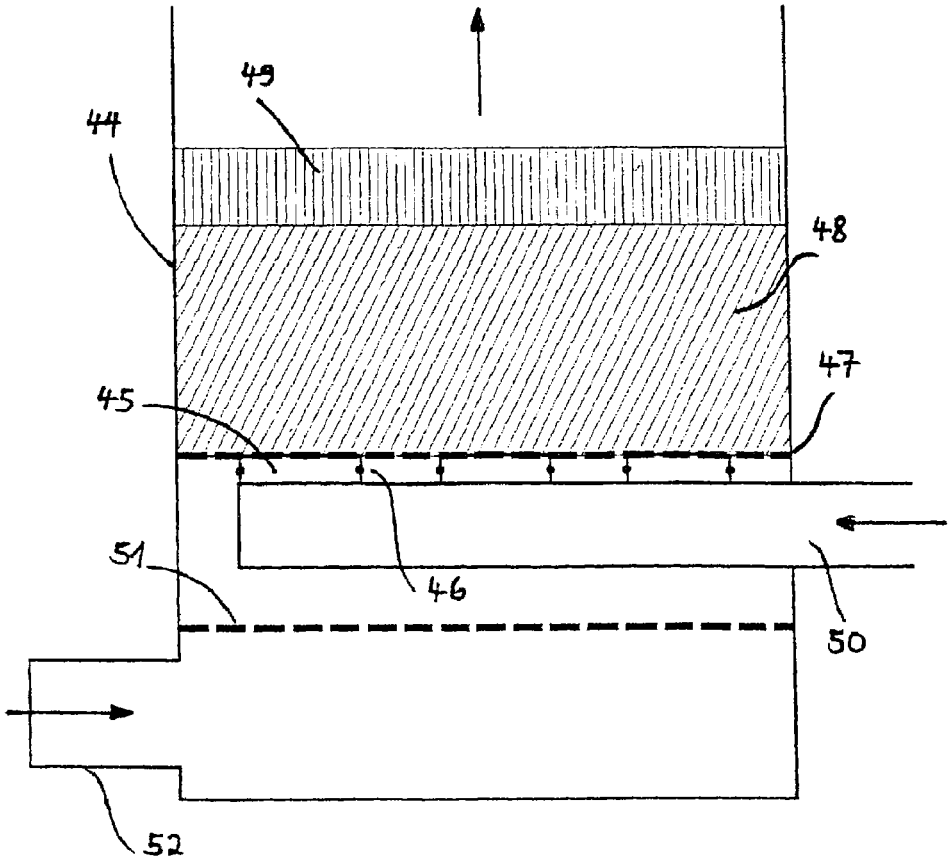
FIG. 17: shaft reactor reproduction
Figure 18:
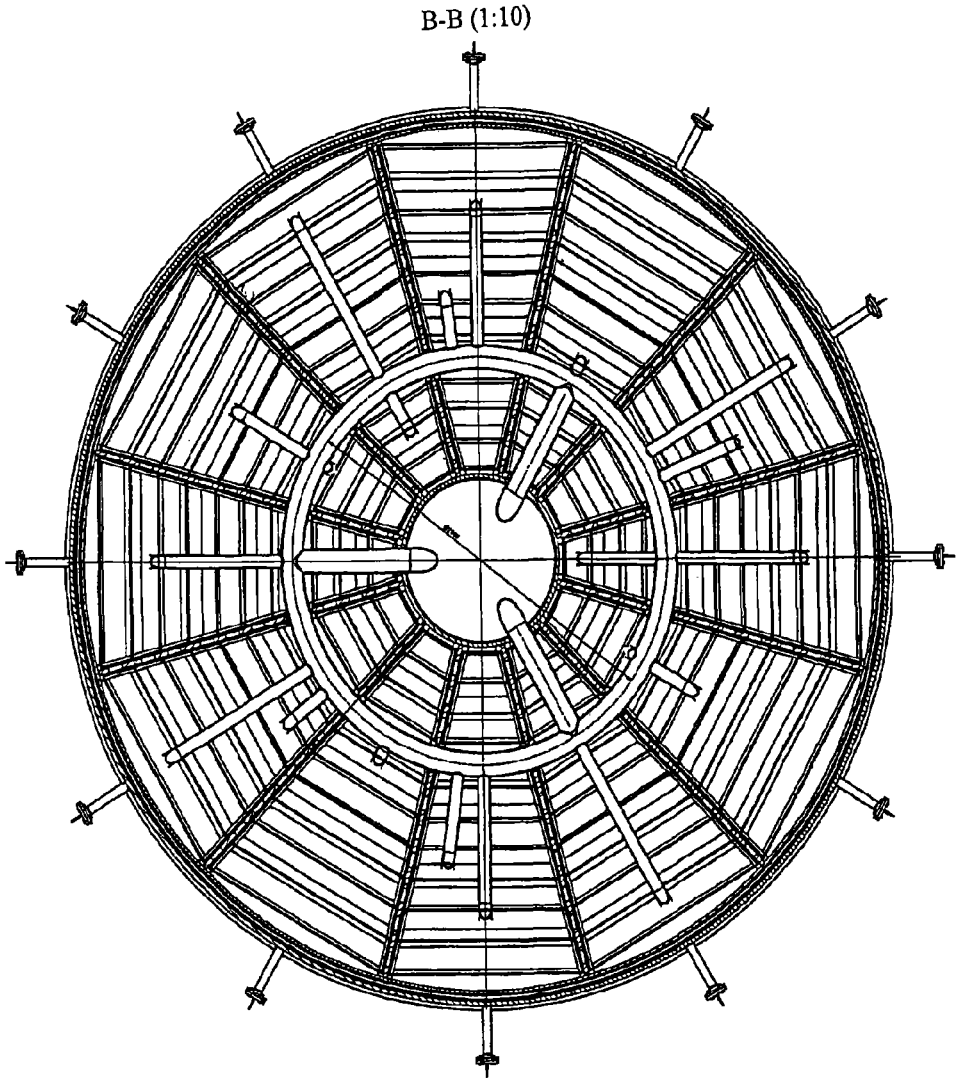
FIG. 18: a schematic of a metering polygon structure.

A longitudinal section of the cuboidal reactor reproduction is shown by FIG. 17.

U.S. provisional patent application No. 60/787,165, filed Mar. 30, 2006, and U.S. provisional patent application No. 60/791,207, filed Apr. 12, 2006, are incorporated into the present application by literature reference. With regard to the abovementioned teachings, numerous changes and deviations from the present invention are possible. It can therefore be assumed that the invention, within the scope of the appended claims, can be performed differently from the way described specifically herein.

What is claimed is:

1. A process for heterogeneously catalyzed partial dehydrogenation of at least one hydrocarbon, the process comprising:

passing through a fixed catalyst bed the entirety of a reaction gas mixture input stream comprising molecular oxygen, molecular hydrogen and the at least one hydrocarbon to be dehydrogenated, wherein the fixed catalyst bed is disposed in a shaft with a given cross section and comprises in the flow direction of the reaction gas mixture input stream an inert bed of the length X of inert shaped bodies followed by a catalytically active bed, wherein the catalytically active bed comprises at least one shaped catalyst body which in the reaction gas mixture input stream causes, at least in the entrance region of the catalytically active bed, a lower activation energy to conduct a combustion reaction of molecular hydrogen with molecular oxygen to yield water and/or a combustion reaction of hydrocarbon with molecular oxygen to yield carbon oxides and water followed by the dehydrogenation of the at least one hydrocarbon to at least one dehydrogenated hydrocarbon, with the proviso that a portion of the at least one hydrocarbon to be dehydrogenated is dehydrogenated to the at least one dehydrogenated hydrocarbon, and the reaction gas mixture input stream is obtained in the shaft by metering an input gas II, comprising molecular oxygen with a total volume flow rate V2, upstream of the fixed catalyst bed to an input gas stream I which comprises molecular hydrogen and the at least one hydrocarbon to be dehydrogenated and flows within the shaft toward the fixed catalyst bed with a volume flow rate V1 and a flow rate W, wherein the input gas II is metered in the form of input gas II streams flowing out of a plurality of exit orifices A of a line system disposed upstream of the fixed catalyst bed in flow direction of the input gas stream I such that:

a) directions of the majority M of all input gas II streams exiting from the exit orifices A in the theoretical absence of the input gas stream I enclose an angle α of [90±60°] *90±30°* with the flow direction of the input gas stream I;

b) a distance D of the majority M of all exit orifices A from the fixed catalyst bed, based on the flow rate W of the input gas stream I in the shaft, is less than or equal to the induction time J of the reaction gas input mixture multiplied by 2·W;

c) a projection of the centers of the majority M of all exit orifices A in flow direction of the input gas stream I into the projection plane E at right angles to the flow direction of the input gas stream I within the projection plane E gives rise to a number ZA of the exit orifice centers present in any $m^2$ of ≥10 for at least 75% of the projection area covered by the input gas stream I;

d) the individual input gas II streams exiting from the exit orifices A corresponding to the number ZA of exit orifice centers deviate from their numerical mean by not more than 50%;

e) among the number ZA of exit orifices, the distance d from one exit orifice center to the closest exit orifice center is not more than $2\sqrt{1m^2/ZA}$;

f) the V1:V2 ratio is ≥8; and g) a ratio X:d, of the length of the bed X and a distance d is greater than 0.1 and less than 5.

2. The process according to claim 1, wherein the input gas II comprises:

from 0 to 80% by volume of steam, from 10 to 97% by volume of $N_2$ and from 3 to 25% by volume of $O_2$.

3. The process according to claim 1 or 2, wherein the input gas II comprises:

from 15 to 80% by volume of $H_2O$, from 20 to 85% by volume of $N_2$ and from 5 to 25% by volume of $O_2$.

4. The process according to claim 1, wherein the V1:V2 ratio is ≥15.

5. The process according to claim 1, wherein the V1:V2 ratio is ≥20.

6. The process according to claim 1, wherein the longest dimension L of one exit orifice A is from ≥0.1 mm to ≤5 cm.

7. The process according to claim 1, wherein the longest dimension L of one exit orifice A is from ≥1 mm to ≤5 mm.

8. The process according to claim 1, wherein the directions of the majority M of all input gas II streams exiting from the exit orifices A in the theoretical absence of the input gas stream I enclose an angle α of [90±30°] *90±20°* with the flow direction of the input gas stream I.

9. The process according to claim 1, wherein the directions of the majority M of all input gas II streams exiting from the exit orifices A in the theoretical absence of the input gas stream I enclose an angle α of 90±10° with the flow direction of the input gas stream I.

10. The process according to claim 1, wherein the majority M of all exit orifices A fulfills the condition D≤0.5·W·J.

11. The process according to claim 1, wherein the majority M of all exit orifices A fulfills the condition D≤0.2·W·J.

12. The process according to claim 1, wherein ZA≥30.

13. The process according to claim 1, wherein ZA≥50.

14. The process according to claim 1, wherein ZA≥100.

15. The process according to claim 1, wherein the distance d is not more than $1.5\sqrt{1m^2/ZA}$.

16. The process according to claim 1, wherein the distance d is not more than $\sqrt{1m^2/ZA}$.

17. The process according to claim 1, wherein the individual input gas II streams exiting from the exit orifices A corresponding to the number ZA of exit orifice centers deviate from their numerical mean by not more than 30%.

18. The process according to claim 1, wherein the individual input gas II streams exiting from the exit orifices A corresponding to the number ZA of exit orifice centers deviate from their numerical mean by not more than 10%.

19. The process according to claim 1, wherein the majority M of all exit orifices A and of the individual input gas II streams exiting from them is understood to mean those exit orifices A and the individual input gas II streams exiting from them from which a total of more than 70% of the total volume flow rate V2 exit, with the proviso that the individual input gas II streams exiting from them, among the entirety of all individual input gas II streams, do not comprise a stream which is smaller than the largest of the individual input gas II streams *not* included in this majority M.

20. The process according to claim 1, wherein the majority M of all exit orifices A and of the individual input gas II streams exiting from them is understood to mean those exit orifices A and the individual input gas II streams exiting from them from which a total of just more than 90% of the total volume flow rate V2 exit, with the proviso that the individual input gas II streams exiting from them, among the entirety of all individual input gas II streams, do not comprise a stream which is smaller than the largest of the individual input gas II streams *not* included in this majority M.

21. The process according to claim 1, wherein a projection of the centers M of all exit orifices A in the flow direction of the input gas stream I into the projection plane E at right angles to the flow direction of the input gas stream I within the projection plane E gives rise to a number ZA of the exit orifice centers present in any $m^2$ of ≥10 for at least 85% of the projection area covered by the input gas stream I.

22. The process according to claim 1, wherein a projection of the centers M of all exit orifices A in flow direction of the input gas stream I into the projection plane E at right angles to the flow direction of the input gas stream I within the projection plane E gives rise to a number ZA of the exit orifice centers present in any $m^2$ of ≥10 for at least 95% of the projection area covered by the input gas stream I.

23. The process according to claim 1, wherein the reaction gas mixture input stream is conducted through the fixed catalyst bed with the proviso that at least 2 mol % of the at least one hydrocarbon to be dehydrogenated present therein is dehydrogenated to the at least one dehydrogenated hydrocarbon.

24. The process according to claim 1, wherein the reaction gas mixture input stream is conducted through the fixed catalyst bed with the proviso that at least 5 mol % of the at least one hydrocarbon to be dehydrogenated present therein is dehydrogenated to the at least one dehydrogenated hydrocarbon.

25. The process according to claim 1, wherein the reaction gas mixture input stream comprises at least 5% by volume of the at least one hydrocarbon to be dehydrogenated.

26. The process according to claim 1, wherein the reaction gas mixture input stream comprises at least 10% by volume of the at least one hydrocarbon to be dehydrogenated.

27. The process according to claim 1, wherein the molar content of molecular oxygen in the reaction gas mixture input stream is not more than 50 mol % of a molar amount of molecular hydrogen present therein.

28. The process according to claim 1, wherein, as the reaction gas mixture input stream passes through the fixed catalyst bed, at least 95 mol % of the total amount of molecular oxygen present in the reaction gas mixture input stream is consumed for the combustion of the molecular hydrogen present in the reaction gas mixture input stream.

29. The process according to claim 1, wherein the temperature of the reaction gas mixture input stream on entry into the fixed catalyst bed is from 300 to 700° C.

30. The process according to claim 1, wherein the loading on the fixed catalyst bed, based on the total amount of a catalyst present therein, with the at least one hydrocarbon to be dehydrogenated is from 100 to 10 000 1 (STY)/l·h.

31. The process according to claim 1, wherein the induction time J is ≤2000 ms.

32. The process according to claim 1, wherein the induction time J is ≤100 ms.

33. The process according to claim 1, wherein the cross section of the lines conducting the input gas II is polygonal where the exit orifices A are disposed.

34. The process according to claim 1, wherein the cross section of the lines conducting the input gas II is tetragonal where the exit orifices A are disposed.

35. The process according to claim 1, wherein the exit orifices A are round.

36. The process according to claim 1, wherein the temperature difference $\Delta T_{II}^{I}$ between the temperature of the input gas stream I and the temperature of the input gas II is not greater than 300° C.

37. The process according to claim 1, wherein the at least one hydrocarbon to be dehydrogenated is propane.

38. The process according to claim 1, wherein the at least one dehydrogenated hydrocarbon is propylene.

39. The process according to claim 1, which is performed in a shaft reactor configured as a tray reactor.

40. The process according to claim 1, wherein the process for heterogeneously catalyzed partial dehydrogenation of the at least one hydrocarbon is followed by a process for heterogeneously catalyzed partial oxidation of the at least one dehydrogenated hydrocarbon.

41. The process according to claim 40, wherein the downstream process for heterogeneously catalyzed partial oxidation of the at least one dehydrogenated hydrocarbon is a process for heterogeneously catalyzed partial oxidation of propylene to acrolein and/or acrylic acid.

42. The process according to claim 41, wherein the acrylic acid is removed from the product gas mixture of the heterogeneously catalyzed partial oxidation in such a way that the product gas mixture [which may, if appropriate, have been cooled beforehand by direct and/or indirect cooling] is fractionally condensed in a column comprising separating internals with a side draw removal of crude acrylic acid and/or subjected to an absorption with water or an aqueous solution.

43. The process according to claim 42, which is followed by a process for suspension crystallization of the crude acrylic acid.

44. The process according to claim 43, which is followed by a process for washing the acrylic acid suspension crystals formed in a wash column.

45. The process according to claim 44, which is followed by a process in which washed acrylic acid suspension crystals are melted and polymerized to polymers.

*46. The process according to claim 42, where the product gas mixture is cooled beforehand by direct and/or indirect cooling before removal of acrylic acid from the product gas mixture of the heterogeneously catalyzed partial oxidation.*

* * * * *